US012569576B2

(12) United States Patent
Sharma

(10) Patent No.: US 12,569,576 B2
(45) Date of Patent: Mar. 10, 2026

(54) COMPOSITIONS AND METHODS FOR MEASURING OXIDATIVE STRESS

(71) Applicant: Washington University, St. Louis, MO (US)

(72) Inventor: Vijay Sharma, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/344,739

(22) Filed: Jun. 10, 2021

(65) Prior Publication Data

US 2021/0386874 A1 Dec. 16, 2021

Related U.S. Application Data

(60) Provisional application No. 63/037,219, filed on Jun. 10, 2020.

(51) Int. Cl.
*A61K 51/04* (2006.01)

(52) U.S. Cl.
CPC ...... *A61K 51/0459* (2013.01); *A61K 51/0482* (2013.01)

(58) Field of Classification Search
CPC ........................ A61K 51/0459; A61K 51/0482
USPC ........................................................ 424/1.65
See application file for complete search history.

(56) References Cited

U.S. PATENT DOCUMENTS

| | | | | |
|---|---|---|---|---|
| 8,652,442 B2 * | 2/2014 | Piwnica-Worms | ...... | C12Q 1/28<br>424/9.6 |
| 2010/0029909 A1 * | 2/2010 | Sukerkar | ................ | A61K 49/10<br>324/309 |
| 2011/0250145 A1 * | 10/2011 | Sharma | .................... | C12Q 1/28<br>424/9.6 |

OTHER PUBLICATIONS

Wang et al. Sci. Rep. 2017, 7, 1-11. (Year: 2017).*
Wang et al. Sci Rep. 2017, 7 (supp), 1-11. (Year: 2017).*
Srivastava et al. BLN-27794 Brookhaven National Lab. 1980, 1-21. (Year: 1980).*
Shao et al. Molecules 2014, 19, 11600-11612. (Year: 2014).*
Price et al. Chem. Soc. Rev. 2014, 43, 260-290. (Year: 2014).*
Wadas et al. Mag. Res. Med. 2010, 64, 1274-1280. (Year: 2010).*
Kim et al. Bioorg. Med. Chem. Lett. 24 (2015) 2056-2059. (Year: 2015).*
Lang et al. Bioconjugate Chem. 2011, 22, 2415-2422. (Year: 2011).*
Agarwal, A., et al., "Chemiluminescence Technique for Measuring Reactive Oxygen Species," 2004, Reprod Biomed Online, 9:466-468.
Al-Karmi, S., et al., "Preparation of an (18) F-Labeled Hydrocyanine Dye as a Multimodal Probe for Reactive Oxygen Species," 2017, Chemistry 23, 254-258.
Anderson, C.J., et al., "Copper-64 Radiopharmaceuticals for PET Imaging of Cancer: Advances in Preclinical and Clinical Research," 2009, Cancer Biother Radiopharm, 24/4:379-393.
Bedouhene, S., et al., "Luminol-amplified Chemiluminescence Detects Mainly Superoxide Anion Produced by Human Neutrophils," 2017, Am J Blood Res, 7/4:41-48.
Carroll, V., et al., "A Boronate-caged [18F]FLT Probe for Hydrogen Peroxide Detection Using Positron Emission Tomography," 2014, JACS, 136:14742-14745.
Chen, K., et al., "Design and Development of Molecular Imaging Probes," 2010, Curr Top Med Chem, 10/12:1227-1236.
Chen, X., et al., "Fluorescent and Luminescent Probes for Detection of Reactive Oxygen and Nitrogen Species," 2011, Chem Soc Rev, 40:4783-4804.
Chu, W., et al. "Development of a PET Radiotracer for Non-Invasive Imaging of the Reactive Oxygen Species, Superoxide, in vivo," 2014, Organic & Biomolecular Chemistry 12/25:4421-4431.
Chuang, C.Y., et al., "Lipopolysaccharide Induces Apoptotic Insults to Human Alveolar Epithelial A549 Cells Through Reactive Oxygen Species-Mediated Activation of an Intrinsic Mitochondrion-Dependent Pathway," 2011, Arch Toxicol, 85:209-218.
Dickinson, B.C., et al., "A Nuclear-localized Fluorescent Hydrogen Peroxide Probe for Monitoring Sirtuin-mediated Oxidative Stress Responses in vivo," 2011, Chem. Biol. 18, 943-948.
Dickinson, B.C., et al., "A Palette of Fluorescent Probes with Varying Emission Colors for Imaging Hydrogen Peroxide Signaling in Living Cells," 2010, JACS, 132:5906-5915.
Dodeigne, C., et al., "Chemiluminescence as Diagnostic Tool. A Review," 2000, Talanta ,51:415-439.
Dunn et al., A Practical Guide to Evaluating Colocalization in Biological Microscopy, 2011, Am J Physiol Cell Physiol, 300:C723-C742.
Elhai, J., et al., "[83] Conjugal Transfer of DNA to Cyanobacteria," 1988, Methods in Enzymology, 167:747-754.
Grailer, J.J., et al., "Critical Role for the NLRP3 Inflammasome During Acute Lung Injury," 2014, J Immunol, 192:5974-5983.
Herrero, R., et al., "New Insights into the Mechanisms of Pulmonary Edema in Acute Lung Injury," 2018, Ann Transl Med .6/32, 17 pages.
Irwin, J., et al., "ZINC - A Free Database of Commercially Available Compounds for Virtual Screening," 2005, J Chem Inf Model, 45:177-182.
Ishii, M., et al., "SIN-1-induced Cytotoxicity in Cultured Endothelial Cells Involves Reactive Oxygen Species and Nitric Oxide: Protective Effect of Sepiapterin," 1999, J Cardiovasc Pharmacol, 33:295-300.

(Continued)

*Primary Examiner* — Michael G. Hartley
*Assistant Examiner* — Sean R Donohue
(74) *Attorney, Agent, or Firm* — Stinson LLP

(57) ABSTRACT

The present disclosure provides for imaging agents and methods of making and using the same. The imaging agent comprises a luminol component comprising a luminol moiety or functional analogue thereof; a chelator; a linker group bonding or complexing the luminol component to the chelator; and a radiolabel component bound to the chelator. The imaging agent described herein is capable of monitoring, targeting, or imaging oxidative stress, reactive oxygen species (ROS), superoxide generation, or hydrogen peroxide generation, mediating pathophysiology of different disease states.

20 Claims, 22 Drawing Sheets
(16 of 22 Drawing Sheet(s) Filed in Color)

(56) References Cited

OTHER PUBLICATIONS

Jakic, B., et al., Elevated Sodium Leads to the Increased Expression of HSP60 and Induces Apoptosis in HUVECs, 2017, PloS One, e0179383, 15 pages.
Jones, H.A., et al., "In vivo Measurement of Neutrophil Activity in Experimental Lung Inflammation," 1994, Am. J. Respir Crit. Care Med. 149:1635-1639.
Karton-Lifshin, N., et al., "A Unique Paradigm for a Turn-ON Near-Infrared Cyanine-based Probe: Noninvasive Intravital Optical Imaging of Hydrogen Peroxide," 2011, JACS, 133:10960-10965.
Kauffman, M.E., et al., "MitoSOX-Based Flow Cytometry for Detecting Mitochondrial ROS," 2016, React Oxyg Species (Apex) 2, 361-370.
Kubota, C., et al., "Constitutive Reactive Oxygen Epecies Generation from Autophagosome/Lysosome in Neuronal Oxidative Toxicity," 2010, J Biol Chem, 285:667-674.
Lebrecht, D., et al., "Dexrazoxane Prevents Doxorubicin-Induced Long-term Cardiotoxicity and Protects Myocardial Mitochondria from Genetic and Functional Lesions in Rats," 2007, BR J Pharmacol, 151:771-778.
Lipinski, C.A., "Drug-like Properties and the Causes of Poor Solubility and Poor Permeability," 2000, J Pharm Tox Methods, 44:235-249.
Malide, D., et al., "A Fluorescence-based Imaging Method to Measure in vitro and in vivo Mitophagy Using mt-Keima," 2017, Nature Protocols, 12:1576-1587.
Marambio, P., et al., "Glucose Deprivation Causes Oxidative Stress and Stimulates Aggresome Formation and Autophagy in Cultured Cardiac Myocytes," 2010, Biochim Biophy Acta , 1802/6:509-518.
Melcher, R.L., et al., "An Improved Microtiter Plate Assay to Monitor the Oxidative Burst in Monocot and Dicot Plant Cell Suspension Cultures," 2016, Plant Methods, 12:5, 11 pages.
Oliveira, P.J., et al., "Carvedilol-mediated Antioxidant Protection Against Doxorubicin-induced Cardiac Mitochondrial Toxicity," 2004, Toxicol Appl Pharmacol, 200:159-168.
Oliveira, P.J., et al., Carvedilol Inhibits the Exogenous NADH Dehydrogenase in Rat Heart Mitochondria, 2000, Arch Biochem Biophy, 374:279-285.
Peoples, J.N., et al., "Mitochondrial Dysfunction and Oxidative Stress in Heart Disease," 2019, Exp Mol Med, 51:1-13.
Polster, B.M., et al., "Use of Potentiometric Fluorophores in the Measurement of Mitochondrial Reactive Oxygen Species," 2014, Methods Enzymol, 547:225-250.
Quickenden, T.I., et al., "The Forensic Use of Luminol Chemiluminescence to Detect Traces of Blood Inside Motor Vehicles," 2004, Luminescence, 19:271-277.
Rodic, S., et al., "Reactive Oxygen Species (ROS) are a Key Determinant of Cancer's Metabolic Phenotype," 2018, Int. J. Cancer, 142:440-448.
Sadiku, P., et al., "Prolyl Hydroxylase 2 Inactivation Enhances Glycogen Storage and Promotes Excessive Neutrophilic Responses," 2017, J Clin Invest, 127:407-3420.
Si, F., et al., "A Mitochondrion Targeting Fluorescent Probe for Imaging of Intracellular Superoxide Radicals," 2015, Chem Commun (Camb), 51:7931-7934.
Sivapackiam, J., et al., "68Ga-Galmydar: A Pet Imaging Tracer for Noninvasive Detection of Doxorubicin-induced Cardiotoxicity," 2019, PloS One 14, e0215579, 19 pages.
Stauffer, W., et al., "EzColocalization: An Image J Plugin for Visualizing and Measuring Colocalization in Cells and Organisms," 2018, Scientific Reports 8, 15764, 13 pages.
Stockhofe , K., et al., "Radiolabeling of Nanoparticles and Polymers for PET Imaging, " 2014, Pharmaceuticals (Basel), 7/4:392-418.
Stoica, B.A., et al., "Improving Luminol Blood Detection in Forensics," 2016, J Forensic Sci, 61:1331-1336.
Studier, F.W., "Protein Production by Auto-Induction in High-Dnesity Shaking Cultures," 2005, Protein Expr Purif, 41/1:207-234.
Sul, O.J., et al., "Lipopolysaccharide (LPS)-Induced Autophagy Is Responsible for Enhanced Osteoclastogenesis," 2017, Mol. Cells, 40:880-887.
Sundaram, G., et al., "Live-Cell Fluorescence Imaging: Assessment of Thioflavin T Uptake Profiles in Human Epidermal Carcinoma Cells," 2017, Med Chem Commun, 9:946-950.
Tao, Z., et al., "Kinetic Studies on Enzyme-Catalyzed Reactions: Oxidation of Glucose, Decomposition of Hydrogen Peroxide and Their Combination," 2009, Biophys.J, 96/7:2977-2988.
Teague, S.J., et al., "The Design of Leadlike Combinatorial Libraries," 1999, Angewandte Chemie Int Ed Engl, 24, 3943-3948, Abstract Only.
Van De Bittner, G.C., et al., "In vivo Imaging of Hydrogen Peroxide Production in a Murine Tumor Model with a Chemoselective Bioluminescent Reporter," 2010, PNAS, 107/50:21316-21321.
Wilson, A.A., et al., "Evaluation of a Novel Radiotracer for Positron Emission Tomography Imaging of Reactive Oxygen Species in the Central Nervous System," 2017, Nucl Med Biol, 53:14-20.
Werengowska-Ciecwierz, K., et al., "The Chemistry of Bioconjugation in Nanoparticles-Based Drug Delivery System," 2015, Advances in Condensed Matter Physical, vol. 2015, 28 pages.
Zemans, R.L., et al., "Transepithelial Migration of Neutrophils: Mechanisms and Implications for Acute Lung Injury," 2009, Am J Respir Cell Mo Biol, 40:519-535.
Zhao, Y., et al., "Protective Effect of Suberoylanilide Hydroxamic Acid Against Lipopolysaccharide-Induced Liver Damage in Rodents," 2015, J Surg Res 194/2:544-550.
Holik et al., "The Chemical Scaffold of Theranostic Radiopharmaceuticals: Radionuclide, Bifunctional Chelator, and Pharmacokinetics Modifying Linker," Molecules, 27(10):3062, May 2022.
Sneddon et al., "Emerging Chelators for Nuclear Imaging," Curr Opin Chem Biol., 63:152-162, Aug. 2021.

* cited by examiner

DHE

MitoSOX

CM-$H_2$DCFDA

Luminol

DHMT

FDMT

Galuminox 1 2 3 4

X = F, $^{18}F$, I, $^{123}I$, $^{131}I$

Y = O, S

M = Ga, $^{68}$Ga, $^{67}$Ga
Y = O, S

1

2

3

4

M = Ga, Fe, In, Cu, Gd, Trivalent Lanthanide, $^{67/68}$Ga $^{64}$Cu, $^{111}$In

Y = O, S

M = Ga, Fe, In, Cu, Gd or Trivalent Lanthanide, $^{67/68}Ga$ $^{64}Cu$, $^{111}In$

Y = O, S

LPS Post 24h Saline Control

COMPOSITIONS AND METHODS FOR MEASURING OXIDATIVE STRESS

CROSS-REFERENCE TO RELATED APPLICATIONS

This application claims benefit of U.S. Provisional Application Ser. No. 63/037,219 filed Jun. 10, 2020, the entire disclosure of which are incorporated herein by reference.

STATEMENT REGARDING FEDERALLY SPONSORED RESEARCH OR DEVELOPMENT

This invention was made with government support under HL111163, EB025815, and HL142297 awarded by the National Institutes of Health. The government has certain rights in the invention.

FIELD OF THE INVENTION

The present disclosure generally relates to various compositions and methods of using these compositions for monitoring, targeting, and imaging oxidative stress using, for example, positron emission tomography or single photon emission computed tomography

SUMMARY OF THE INVENTION

Among the various aspects of the present disclosure is the provision of imaging agents and methods of making and using same, wherein the imaging agent comprises a luminol component comprising a luminol moiety or functional analogue thereof; a chelator (e.g., a NOTA-containing moiety); a linker group (e.g., a bond, glycine) bonding or complexing the luminol component to the chelator; and a radiolabel component (e.g., $^{68}$Ga) bound to or within the chelator. The imaging agent described herein is capable of monitoring, targeting, or imaging oxidative stress, reactive oxygen species (ROS), superoxide generation, or hydrogen peroxide generation.

Other objects and features will be in part apparent and in part pointed out hereinafter.

DESCRIPTION OF THE DRAWINGS

The patent or application file contains at least one drawing executed in color. Copies of this patent or patent application publication with color drawings will be provided by the Office upon request and payment of the necessary fee. The disclosure will be better understood, and features, aspects and advantages other than those set forth above will become apparent when consideration is given to the following detailed description thereof. Such detailed description makes reference to the following drawings, wherein.

DETAILED DESCRIPTION OF THE INVENTION

Figure 1:
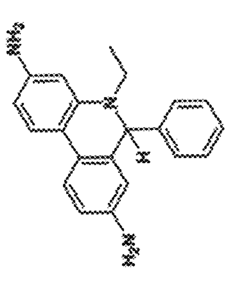
FIG. 1 depicts the chemical structures of ROS probes.
Figure 1:
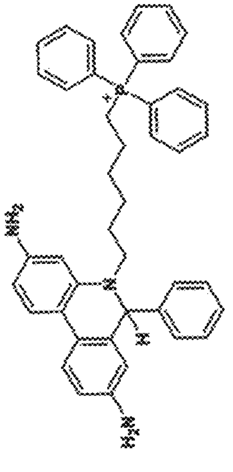
Figure 1:
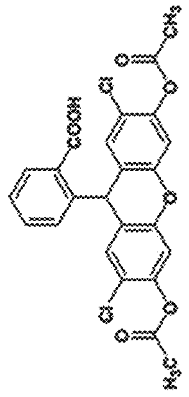
Figure 1:
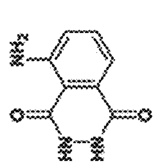
Figure 1:
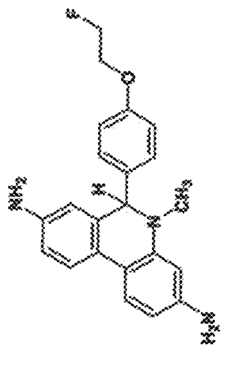
Figure 1:
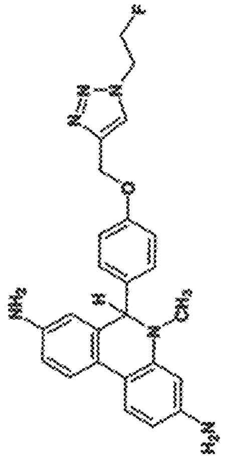
Figure 1:
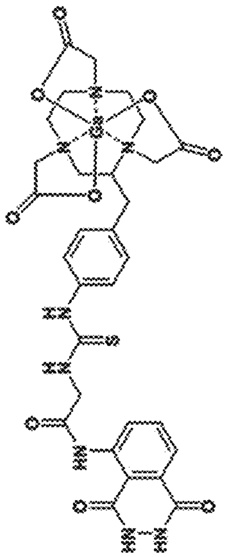

Described herein are imaging agents (e.g., PET and SPECT tracers) for noninvasive imaging/detecting of reactive oxygen species (ROS) and various precursors thereof along with various methods of preparing and using these agents and precursors.

The present disclosure is based, at least in part, on the discovery that imaging agents (e.g., Galuminox, as referred to herein) comprising a luminol component comprising a luminol moiety or functional analogue thereof; a chelator (e.g., a NOTA-containing moiety); a linker group (e.g., a bond, glycine) bonding or complexing the luminol component to the chelator; and a radiolabel component (e.g., $^{68}Ga$) bound to or within the chelator is a moderately fluorescent probe and is useful for detecting superoxide and hydrogen peroxide generation. It has been discovered that these agents are highly sensitive for detecting ROS. For example, Galuminox can be detected in micro-doses, reducing the potential for toxicity.

The imbalance in production/mitigation of reactive oxygen species (ROS) has been implicated in the pathogenesis of numerous diseases, such as cardiovascular disease, diabetes, atherosclerosis, asthma, Alzheimer's disease, psoriasis, rheumatoid arthritis, aging, acute lung injury (ALI), chronic lung allograft dysfunction, systemic lupus erythematosus (SLE), kidney disease, and various cancers such as breast cancer.

We have discovered a series of imaging agents including, Galuminox, a moderately fluorescent probe that detects superoxide and hydrogen peroxide generation. Using live fluorescence imaging analysis, Galuminox demonstrates the ability to monitor effects of ROS-attenuating agents, such as Carvedilol, Dexrazoxane, and mitoTempo in lung epithelial A549 cells. Dynamic PET/CT scans 45 minutes post tail-vein administration of $^{68}Ga$-Galuminox show 4-fold higher uptake and stable retention in lungs of LPS treated mice compared to their saline-only treated counterparts. Post preclinical PET imaging, quantitative biodistribution studies also correlate with 4-fold higher retention of the radiotracer in lungs of LPS treated mice compared with their saline-only treated control counterparts. Consistent with these observations, lung cells isolated from LPS-treated mice demonstrated elevated ROS production deploying CellROX, the ROS probe. Finally, Galuminox uptake correlates with histological and physiological evidence of acute lung injury as evident by polynuclear infiltration, thickening of the alveolar epithelial membranes and increased bronchioalveolar lavage protein content. Taken collectively, these data indicate that $^{68}Ga$-Galuminox tracer uptake is a measure of ROS activity in acutely injured lungs and suggests its potential utility in monitoring oxidative stress in other diseases.

Because over production of reactive oxygen species has been implicated in the pathogenesis of numerous diseases, such as cardiovascular disease, diabetes, atherosclerosis, asthma, Alzheimer's disease, psoriasis, rheumatoid arthritis, acute lung injury (ALI), chronic lung allograft dysfunction, systemic lupus erythematosus (SLE), kidney disease, and various cancers such as breast cancer, carefully crafted sensitive and specific PET and SPECT tracers would provide noninvasive imaging tools in diagnostic nuclear medicine at the molecular level. Given the role of ROS pathway in inflammation, these imaging agents would also be beneficial in stratification of therapeutic choices including offering tools for evaluation of therapeutic efficacy for ROS scavengers in vivo.

As noted, various imaging agents of the present invention generally comprise: a luminol component comprising a luminol moiety or functional analogue thereof; a chelator; a linker group bonding or complexing the luminol component to the chelator; and a radiolabel component bound to or within the chelator. A general formula of the imaging agents can be as follows:

A-B—C-D where A is the luminol component, B is the linker group, C is the chelator, and D is the radiolabel component bound to or within the chelator. The components of the imaging agents are discussed in detail below. Although the imaging agents have been described as comprising a radiolabel component, the present invention also includes corresponding non-radiolabeled analogs of the imaging agents, various precursors thereof, and progeny of the imaging agents. Non-radiolabeled analogs of the imaging agents have the same chemical components as the imaging agents except that D is not a radioisotope.

Luminol Component

The imaging agent as described herein comprises a luminol component comprising a luminol moiety, formula (I), or functional analogue thereof. A functional analogue of luminol can have the base luminol structure with one or more substitutions and wherein the imaging agent comprising a luminol analogue retains ROS sensing or detecting activity.

(I)

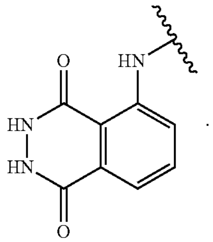

Radiolabel Component

As described herein, the imaging agent comprises a radiolabel component, such as a positron emitting isotope (e.g., $^{68}Ga$) or photon emitting isotope (e.g., $^{67}Ga$). In some embodiments, the radiolabel component is suitable for use in PET imaging or SPECT imaging. Typically, the radiolabel component comprises a synthetic radioisotope. In various embodiments, the radiolabel component comprises at least one radioisotope selected from the group consisting of $^{2}H$ (D or deuterium), $^{3}H$ (T or tritium), $^{11}C$, $^{13}C$, $^{14}C$, $^{13}N$, $^{15}N$, $^{14}O$, $^{15}O$, $^{17}O$, $^{18}O$, $^{18}F$, $^{22}Na$, $^{26}Al$, $^{35}S$, $^{36}Cl$, $^{38}K$, $^{40}K$, $^{44}Sc$, $^{52}Fe$, $^{55}Co$, $^{62}Zn$, $^{63}Zn$, $^{63}Zn$, $^{61}Cu$, $^{62}Cu$, $^{64}Cu$, $^{67}Cu$, $^{67}Ga$, $^{68}Ga$, $^{68}Ge$, $^{70}As$, $^{71}As$, $^{74}As$, $^{75}Br$, $^{76}Br$, $^{77}Br$, $^{82}Br$, $^{82}Rb$, $^{89}Zr$, $^{89}Sr$, $^{86}Y$, $^{90}Y$, $^{94}Tc$, $^{99m}Tc$, $^{110}In$, $^{111}In$, $^{122}Xe$, $^{120}I$, $^{121}I$, $^{123}I$, $^{124}I$, $^{125}I$, $^{131}I$, $^{153}Sm$, $^{153}Gd$, $^{155}Tb$, $^{177}Lu$, $^{186}Re$, $^{188}Re$, and $^{201}Tl$.

In some embodiments, the radiolabel component is suitable for use in PET imaging. For example, the radiolabel component comprises at least one isotope (e.g., positron emitting isotope) selected from the group consisting of $^{14}O$, $^{15}O$, $^{13}N$, $^{11}C$, $^{18}F$, $^{22}Na$, $^{26}Al$, $^{82}Rb$, $^{38}K$, $^{62}Cu$, $^{63}Zn$, $^{70}As$, $^{68}Ga$, $^{44}Sc$, $^{61}Cu$, $^{52}Fe$, $^{62}Zn$, $^{63}Zn$, $^{64}Cu$, $^{86}Y$, $^{76}Br$, $^{55}Co$, $^{71}As$, $^{74}As$, $^{68}Ge$, $^{40}K$, $^{121}I$, $^{120}I$, $^{110}In$, $^{94}Tc$, $^{122}Xe$, $^{89}Zr$, and $^{124}F$ In various embodiments, the radiolabel component comprises at least one isotope selected from the group consisting of $^{18}F$, $^{64}Cu$, $^{44}Sc$, and $^{68}Ga$. In preferred embodiments, the radiolabel component comprises $^{68}Ga$. In other embodiments, the radiolabel component comprises aluminum fluoride ($Al^{18}F$). Aluminum fluoride can have the advantage of being an $^{18}F$ tracer and can be compatible with both metal and halogen radionuclides. In further embodiments, the radiolabel component comprises $^{64}Cu$.

In some embodiments, the radiolabel component is suitable for use in SPECT imaging. As such, in some embodiments, the radiolabel component comprises a photon emitting isotope (e.g., $^{67}Ga$, $^{99m}Tc$, $^{111}In$, $^{123}I$, and $^{131}I$).

Examples of suitable, non-limiting radiolabel groups can be: $^{2}H$ (D or deuterium), $^{3}H$ (T or tritium), $^{11}C$, $^{13}C$, $^{14}C$, $^{64}Cu$, $^{44}Sc$, $^{67}Cu$, $^{13}N$, $^{15}N$, $^{15}O$, $^{17}O$, $^{18}O$, $^{18}F$, $^{89}Sr$, $^{35}S$, $^{153}Sm$, $^{36}Cl$, $^{82}Br$, $^{75}Br$, $^{76}Br$, $^{77}Br$, $^{123}I$, $^{124}I$, $^{125}I$, $^{131}I$, $^{111}In$, $^{67}Ga$, $^{68}Ga$, $^{177}Lu$, $^{186}Re$, $^{188}Re$, $^{201}Tl$, $^{11}Tc$, $^{90}Y$, $^{89}Zr$ as well as various lanthanide and lanthanide-like radioisotopes (e.g., $^{153}Gd$, $^{155}Tb$ and $^{177}Lu$). The radiolabel component can comprise or consist of any one of these radioisotopes.

It is to be understood that an isotopically labeled compound needs only to be enriched with a detectable isotope to, or above, the degree which allows detection with a technique suitable for the particular application, e.g., in a detectable compound labeled with $^{11}C$, the carbon-atom of the labeled group of the labeled compound may be constituted by $^{12}C$ or other carbon-isotopes in a fraction of the molecules. The radionuclide incorporated in the radiolabeled compounds will depend on the specific application of that radiolabeled compound. For example, "heavy" isotope-labeled compounds (e.g., compounds containing deuterons/heavy hydrogen, heavy nitrogen, heavy oxygen, heavy carbon) can be useful for mass spectrometric and NMR based studies. As another example, for in vitro labelling or in competition assays, compounds that incorporate $^{3}H$, $^{14}C$, or $^{125}I$ can be useful. For in vivo imaging applications $^{11}C$, $^{13}C$, $^{18}F$, $^{19}F$, $^{120}I$, $^{123}I$, $^{134}I$, $^{75}Br$, or $^{76}Br$ can generally be useful.

As described herein, the radiolabel can be incorporated with the imaging agent by various methods. For example, the radiolabel can be chelated and incorporated into the binding site of a chelator.

References herein to "radiolabeled" include a compound where one or more atoms are replaced or substituted by an atom having an atomic mass or mass number different from the atomic mass or mass number typically found in nature (e.g., naturally occurring). One non-limiting exception is $^{19}F$, which allows detection of a molecule which contains this element without enrichment to a higher degree than what is naturally occurring. Compounds carrying the substituent $^{19}F$ may thus also be referred to as "labelled" or the like. The term radiolabeled may be interchangeably-used with "isotopically-labelled", "labelled", "isotopic tracer group", "isotopic marker", "isotopic label", "detectable isotope", or "radioligand".

Chelator

As described herein, the imaging agent comprises a chelator for the radiolabel component. For example, chelators for a radiolabel component (e.g., $^{18}F$, $^{64}Cu$, and $^{68}Ga$) can be any of those known in the art (e.g., a macrocyclic chelator). As another example, the chelator can comprise N-hydroxysuccinimidyl S-acetylmercaptoacetyltriglycinate (NHS-MAG3), mercaptoacetyltriglycine (MAG3), diethylenetriaminepentaacetic acid (DTPA), 3p-C-NE3TA, 2-[4,7-Bis(carboxymethyl)-1,4,7-triazonan-1-yl]acetic acid (NOTA), 3p-C-NOTA, 2-[(5S)-4,7-bis(carboxymethyl)-5-[(4-isothiocyanatophenyl)methyl]-1,4,7-triazonan-1-yl]acetic acid (pSCN-Bn-NOTA), 3p-C-DE4TA, N'-methyl-N—[(Z)-[(3Z)-3-[(N-methyl-C-sulfidocarbonimidoyl)hydrazinylidene]butan-2-ylidene]amino]carbamimidothioate (ATSM), tetraazamacrocyclic ligands (e.g., 1,4,7,10-tetraazacyclododecane-1,4,7,10-tetraacetic acid (DOTA)), 1,4,7,10-Tetraazacyclododecane-1,4,7,10-tetraacetic acid mono-N-hydroxysuccinimide ester (DOTA-NHS), S-2-(4-Isothiocyanatobenzyl)-1,4,7,10-tetraazacyclododecane tetraacetic acid (pSCN-Bn-DOTA), S-2-(4-Aminobenzyl)-1,4,7,10-tetraazacyclododecane tetraacetic acid (pNH2-Bn-DOTA), 1,4,8,11-tetraazacyclotetradecane-1,4,8,11-tetraacetic acid (TETA), 1,4,8,11-tetraazacyclotetradecane-1,4,8,11-tetraacetic acid-octreotide (TETA-OC), hexaazamacrobicyclic cage-type ligands (e.g., Sarcophogine chelators), cross-bridged tetraamine ligands (e.g., 4,11-bis(carboxymethyl)-1,4,8,11-tetraazabicyclo[6.6.2]hexadecane (CB-TE2A)), 6-Hydrazinopridine-3-carboxylic acid (Hynic), or Succinimidyl-6-hydrazinopyridine-3-carboxylate (NHS-Hynic). As another example, a radiolabelled (e.g., $^{64}Cu$) chelator can be 2,2',2"-(10-(2-((2-(2,5-dioxo-2,5-dihydro-1H-pyrrol-1-yl)ethyl)amino)-2-oxoethyl)-1,4,7,10-tetraazacyclododecane-1,4,7-triyl)triacetic acid (Maleimido-mono-amide-DOTA).

The radiolabel component can be chelated by any method known in the art. Processes of chelating a radiolabel component (e.g., radioligand) are known; see e.g. Anderson et al., Cancer Biother Radiopharm. 2009 August; 24(4): 379-393; Stockholf et al., Pharmaceuticals (Basel). 2014 April; 7(4): 392-418. Except as otherwise noted herein, therefore, the process of the present disclosure can be carried out in accordance with such processes.

Linker Group

Described herein are linker groups used to attach (e.g., bond or complex) the luminol component to a portion of an imaging agent (e.g., a core, a nanoparticle, a radiolabel, a chelator). A linker can be any composition used for conjugation, for example to a chelator.

A linker group can be any linker group suitable for use in an imaging agent. Linker groups for imaging agents (e.g., molecular probes) are well known (see e.g., Werengowska-Ciećwierz et al., Advances in Condensed Matter Physics, Vol. 2015 (2015); Chen et al., Curr Top Med Chem. 2010; 10(12): 1227-1236). Except as otherwise noted herein, therefore, the processes of the present disclosure can be carried out in accordance with such processes.

For example, the linker can conjugate the luminol component to a chelator. For example, the luminol can be covalently attached to the linker. For example, the linker can comprise a glycine linker (e.g., residue of glycine). As another example, the linker can comprise polyethylene glycol (PEG), thioctic acid-polyethylene glycol-maleimide (TA-PEG-Maleimide), thioctic acid-polyethylene glycol-methylether (TA-PEG-OMe), or thioctic acid-polyethylene glycol (TA-PEG). As another example, a linker can comprise an isothiocyanate group, a carboxylic acid or carboxylate groups, a dendrimer, a dendron, Fluorenylmethyloxycarbonyl-protected-2,3-diaminopropanoic acid (Fmoc-protected-2,3-diaminopropanoic acid, ascorbic acid), a silane linker, minopropyltrimethoxysilane (APTMS), or dopamine. Other covalent coupling methods can use employ the use of 2 thiol groups, 2 primary amines, a carboxylic acid and primary amine, maleimide and thiol, hydrazide and aldehyde, or a primary amine and aldehyde. For example, the linker can be an amide, a thioether, a disulfide, an acetyl-hydrazone group, a polycyclic group, a click chemistry (CC) group (e.g., cycloadditions, for example, Huisgen catalytic cycloaddition; nucleophilic substitution chemistry, for example, ring opening of heterocyclic electrophiles; carbonyl chemistry of the "nonaldol" type, for example, formation of ureas, thioureas, and hydrazones; additions to carbon-carbon multiple bonds, for example, epoxidation and dihydroxylation), or a physical or chemical bond.

As used herein, PEG refers to polyethylene glycol having a molecular weight that is preferably about 20,000 g/mol or less, about 10,000 g/mol or less, about 5,000 g/mol or less, about 1000 g/mol or less, about 500 g/mol or less, or about 250 g/mol or less (e.g., about 200 g/mol).

Preferred Imaging Agents

Examples of some preferred imaging agents include those of formulas (Ha) and (IIb):

(IIa)

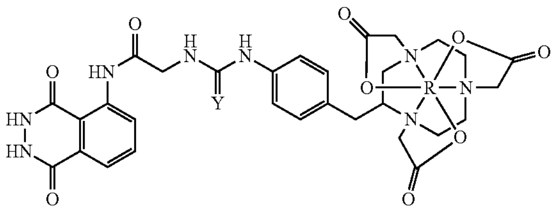

(IIb)

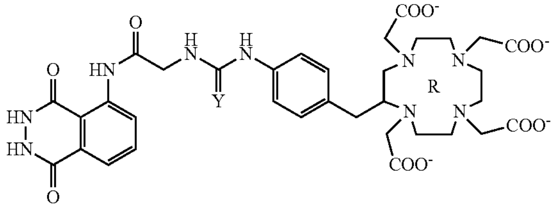

where R is a radiolabel component as described herein and Y is O or S. In formula (IIb), depending upon the oxidation state of the radiolabel component (e.g., metal), then one, two, three, or four of the carboxylic acid groups can form covalent bonds with the radiolabel component (e.g., metal). In various embodiments, R comprises at least one radioisotope selected from the group consisting of $^{2}H$ (D or deuterium), $^{3}H$ (T or tritium), $^{11}C$, $^{13}C$, $^{14}C$, $^{13}N$, $^{15}N$, $^{14}O$, $^{15}O$, $^{17}O$, $^{18}O$, $^{18}F$, $^{22}Na$, $^{26}Al$, $^{35}S$, $^{36}Cl$, $^{38}K$, $^{40}K$, $^{44}Sc$, $^{52}Fe$, $^{55}Co$, $^{62}Zn$, $^{63}Zn$, $^{63}Zn$, $^{61}Cu$, $^{62}Cu$, $^{64}Cu$, $^{67}Cu$, $^{67}Ga$, $^{68}Ga$, $^{68}Ge$, $^{70}As$, $^{71}As$, $^{74}As$, $^{75}Br$, $^{76}Br$, $^{77}Br$, $^{82}Br$, $^{82}Rb$, $^{89}Zr$, $^{89}Sr$, $^{86}Y$, $^{90}Y$, $^{94}Tc$, $^{99m}Tc$, $^{110}In$, $^{111}In$, $^{122}Xe$, $^{120}I$, $^{121}I$, $^{123}I$, $^{124}I$, $^{125}I$, $^{131}I$, $^{153}Sm$, $^{153}Gd$, $^{155}Tb$, $^{177}Lu$, $^{186}Re$, $^{188}Re$, and $^{201}Tl$. In some embodiments, R comprises at least one radioisotope selected from the group consisting of $^{18}F$, $^{64}Cu$, $^{68}Ga$, $^{67}Ga$, $^{99m}Tc$, $^{111}In$, $^{123}I$, and $^{131}I$.

In some embodiments, imaging agents include those of formula (III):

(IIIa)

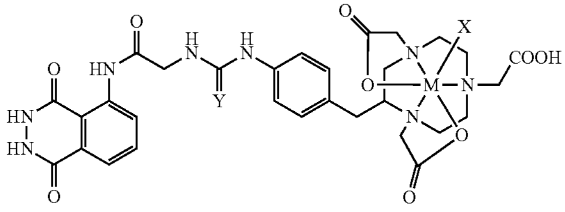

(IIIb)

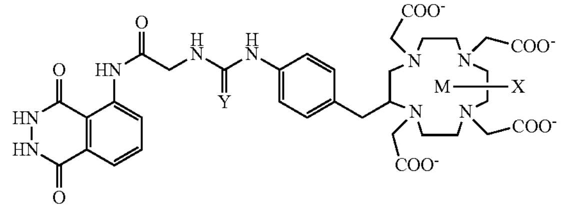

wherein M-X is the radiolabel component where M represents a metal ion and is covalently attached to at least one halogen radioisotope (X), and Y is O or S. In formula (IIIb), depending upon the oxidation state of the radiolabel component (e.g., metal), then one, two, three, or four of the carboxylic acid groups can form covalent bonds with the radiolabel component (e.g., metal). In various embodiments, M comprises a transition metal ion. In various embodiments, M comprises a metal ion of groups 8-13. In various embodiments, M comprises Al ion. In some embodiments, X comprises at least one radioisotope selected from the group consisting of $^{18}F$, $^{36}Cl$, $^{75}Br$, $^{76}Br$, $^{77}Br$, $^{82}Br$, $^{120}I$, $^{121}I$, $^{123}I$, $^{124}I$, $^{125}I$, and $^{131}I$. In some embodiments, M comprises at least one radioisotope selected from the group consisting of $^{18}F$, $^{123}I$, and $^{131}I$.

In certain embodiments, the imaging agent is a compound of the formula below:

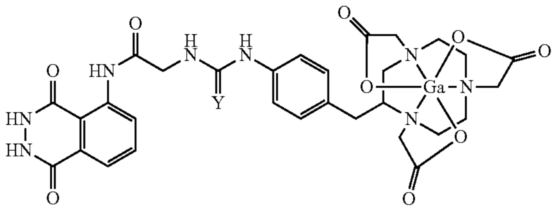

wherein Ga in the formula can be $^{67}Ga$, $^{68}Ga$. In certain embodiments, the imaging agent is Galuminox, which represented by the formula below:

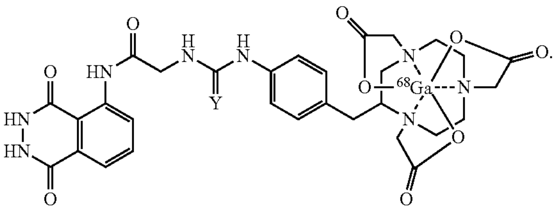

Processes for Preparing an Imaging Agent

Described herein are processes for preparing an imaging agent. The process can comprise: functionalizing the linker group (e.g., a glycine unit) with a chelator, wherein the chelator is functionally attached to the linker group.

Imaging Modalities and Detection Methods

The imaging agents, as described herein, can be contrast agents or radioimaging agents suitable for various imaging approaches, such as MRI (magnetic resonance imaging) and/or PET (positron emission tomography) imaging. The imaging agents can also be contrast agents or radioimaging agents suitable for single-photon emission computerized tomography (SPECT) and PET-MRI imaging.

As described herein, diagnostic imaging has contributed to improved and early detection of a wide range of pathologies in patients. Imaging is central to preclinical testing and animal models developed for translation. Two key features of diagnostic medical imaging tools are the abilities to spatially localize biomarkers without surgical intervention and with potentially higher sensitivity and specificity compared to analysis of biological samples or biofluids.

Positron Emission Tomography (PET)

High-resolution imaging can reveal new microstructural and physiologic features that guide an understanding of heterogeneous disease and responses to therapies. With the current focus on tailoring therapies to individual patients, there is also a need for diagnostic tools that report on pathology at the cellular and molecular level. This typically involves a combination of exogenous contrast agents and radiological imaging. Several radiological imaging modalities, including positron emission tomography (PET), rely completely on exogenous agents for signal. For PET, radioimaging agents are often highly translatable because positron emission is detected in trace doses, allowing for limited toxicity and rapid regulatory approval.

One aspect of the present disclosure provides for a method of detection of a luminol functionalized imaging agent in a subject. The method of detection can employ any number of imaging modalities known in the art. The specific imaging modality will depend on the target tissue or organ in the subject for which the method of detection is being is used. For example, the method of detection can employ PET or PET-MRI (or only MRI) to detect the imaging agent. As another example, the method of detection can employ single-photon emission computed tomography (SPECT) to detect the contrast or imaging agent.

Magnetic Resonance Imaging (MRI)

Magnetic resonance imaging (MRI), in particular, has received attention because of its outstanding spatial resolution in soft tissue and lack of ionizing radiation, allowing new MRI contrast techniques to be rapidly translated for use in the clinic. The luminol functionalized imaging agent can comprise a magnetic resonance imaging agent, such as gadolinium.

Methods of Use

In various embodiments, the imaging agents described herein may be used to image ROS in a subject in need thereof. In general, the method for imaging a target in a subject comprises administering a detectable amount of the imaging agent to the subject and imaging the target using positron emission tomography (PET) and/or magnetic resonance imaging (MRI). Advantageously, the imaging agents provided herein can be used for both MRI and PET imaging.

A method of imaging a target in a subject is provided herein, the method can comprise administering the imaging agent provided herein, or prepared as described herein, to the subject, and imaging the target. For example, the method can comprise imaging ROS using positron emission tomography (PET), magnetic resonance imaging (MRI), PET-MRI, or single-photon emission computer tomography (SPECT). The method can also further comprise quantifying the imaged ROS.

Targets for Imaging

Suitable targets for imaging ROS using the imaging agents provided herein include an organ or organ system in a mammal, such as humans. For example, the target can comprise a lung or lung cell.

Diseases, Disorders, and Conditions Associated with Generation of Reactive Oxygen Species (ROS)

This disclosure provides molecularly specific diagnostic agents capable of noninvasively imaging ROS in subjects being treated for, having, or being suspected of having a disease, disorder, or condition associated with ROS (e.g. ROS mediated pathophysiology). This imaging can be used to monitor for disease progression, including before and/or after treatment. In various embodiments, the subject is being treated for, has, or is suspected of having inflammation, ischemia, tissue injury, acute lung injury, chronic lung allograft dysfunction, oxidative stress-induced inflammation within lungs, and/or oxidative stress in other diseases comprising tissue inflammation, cardiovascular disease, diabetes, atherosclerosis, asthma, Alzheimer's disease, psoriasis, rheumatoid arthritis, systemic lupus erythematosus (SLE), kidney disease, aging, cancer, or breast cancer.

Superoxides can originate from numerous sources in vivo, including the mitochondrial electron transport chain and NADPH oxidase(s), which are activated under conditions of inflammation, ischemia, tissue injury (e.g., acute lung injury), chronic lung allograft dysfunction, oxidative stress-induced inflammation within lungs, systemic lupus erythematosus (SLE), kidney disease or oxidative stress in other diseases. Overproduction of reactive oxygen species (ROS) is a well-established indicator of ongoing tissue inflammation. Production and/or mitigation of ROS has been implicated in the pathogenesis of numerous diseases, such as cardiovascular disease, diabetes, atherosclerosis, asthma, Alzheimer's disease, psoriasis, rheumatoid arthritis, aging, systemic lupus erythematosus (SLE), kidney disease, and various cancers, such as breast cancer.

The imaging agent described herein was shown to have a 4-fold higher uptake and stable retention in lungs of LPS treated mice compared to their saline-only treated counterparts.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a luminol (or functional analogue thereof) conjugated to a chelator with or without a radiolabel, radioisotope, or positron emitting isotope. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms “a” and “an” and “the” and similar references used in the context of describing a particular embodiment (especially in the context of certain of the following claims) can be construed to cover both the singular and the plural, unless specifically noted otherwise. In some embodiments, the term “or” as used herein, including the claims, is used to mean “and/or” unless explicitly indicated to refer to alternatives only or the alternatives are mutually exclusive.

The terms “comprise,” “have” and “include” are open-ended linking verbs. Any forms or tenses of one or more of these verbs, such as “comprises,” “comprising,” “has,” “having,” “includes” and “including,” are also open-ended. For example, any method that “comprises,” “has” or “includes” one or more steps is not limited to possessing only those one or more steps and can also cover other unlisted steps. Similarly, any composition or device that “comprises,” “has” or “includes” one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., “such as”) provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

This example describes the materials and methods used in the rest of the examples.

Chemistry Reagents and General Methods

All reagents were purchased from Sigma-Aldrich, unless otherwise stated. $^1H$ NMR was recorded on Bruker (400 MHz) spectrometer; chemical shifts are reported in δ (ppm) with reference to TMS. Mass analyses were performed using Agilent 1200 HPLC, 1956 MSD (column Shim-pack XR-ODS 30 mm×3.0 mm, 2.2 μm) operating in ES (+) ionization mode. All HPLC analysis was performed with a Waters System 600 equipped with dual λ detector 2487 (set to 280 and 214 nm) and a γ-detector (Bioscan) for identification of radio-peaks. For radio-TLC analysis, silica gel plates were scanned using Bioscan 2000 system.

Chemical Synthesis

Synthesis of Precursor Ligand (LG-NOTA)

Luminol-glycine (LG; 0.18 mmol) and p-SCN-Bn-NOTA (0.18 mmol) were dissolved in dimethylformamide (5 mL) and freshly distilled trimethylamine (100 μL) was added. The contents were mixed and stirred at 50° C. for 15 h. Following completion of the reaction, the precursor ligand was precipitated by addition of ethyl acetate, precipitates were filtered, washed with ethyl acetate (3×5 mL), followed by diethyl ether, and dried to obtain LG-NOTA (Yield: 105 mg; 0.15 mmol; 83.3%). $^1H$ NMR: (400 MHz, DMSO-$d_6$) δ:13.17 (s, 1H), 10.38 (s, 1H), 8.90 (d, 1H), 8.61 (s, 1H), 7.91 (s, 1H), 7.59 (d, 1H), 7.49 (d, 2H), 7.17 (d, 2H), 4.25 (s, 2H), 3.60-2.60 (m, 19H); MS (ESI): Calcd. for $C_{30}H_{36}N_8O_9S$; 684.23; Found: 685.23.

Synthesis of Ga-LG-NOTA (Galuminox)

To obtain metalloprobe, the LG-NOTA (0.20 mmol) and $GaCl_3$ (0.20 mmol) were dissolved in dry DMSO (2 mL) and heated to 110° C. for 60 min. Following reaction, the product was precipitated by addition of EtOAc, filtered, washed with ethyl acetate, diethyl ether, and dried to obtain Ga-LG-NOTA (Yield: 126 mg; 0.17 mmol; 85%). $^1H$ NMR (400 MHz, DMSO-$d_6$) δ: 13.11 (s, 1H), 11.86 (Br. s, 1H), 10.22 (s, 1H), 8.95 (d, 1H), 8.40 (s, 1H), 7.86 d, 1H), 7.63 (d, 1H), 7.52 (s, 2H), 7.23 (s, 2H), 4.32 (s, 2H), 3.64-2.91 (m, 19H); $^1H$ NMR: MS (ESI): Calcd for $C_{30}H_{33}GaN_8O_9S$; 750.7; Found $(M+K)^+$: 789.7.

Radiochemistry

Radiolabeled $^{68}$Ga-Galuminox was synthesized using a procedure described earlier with slight modifications (D. Mueller, et al. Radiolabeling of DOTA-like conjugated peptides with generator-produced (68)Ga and using NaCl-based cationic elution method. Nat. Protoc., 11 (2016), pp. 1057-1066.). Gallium-68 was eluted from a generator (IGG100-50 M) using 0.1 M HCl (1.1 mL), NaOAc buffer (pH 5, 400 μL) was added to the eluent mixture, the pH was adjusted to 4.5, mixed with a solution of the LG-NOTA ligand (50 μg, 50 μL) dissolved in a solution of 90% ethanol/10% polyethylene glycol 200, and heated at 100° C. for 15 min. The reaction was monitored using radio-TLC. Following completion of the reaction, the reaction mixture was passed through cation exchange column (Phenomenex; Strata-X-C 33 m Polymeric Strong Cation; 30 mg/mL) to remove trace metal impurities and unreacted gallium-68. Finally, $^{68}$Ga-Galuminox was analyzed using radio-HPLC for purity on a C-18 reversed-phase column (Alltima, 3 μm, Rocket 53×7 mm) using an eluent gradient of methanol with 0.1% (v/v) trifluoroacetic acid and water with 0.1% (v/v) trifluoroacetic acid (isocratic 20% methanol in water for 5 min; gradient from 20% to 90% methanol in water from 5 to 40 min, at a flow of 1 mL/min). $^{68}$Ga-Galuminox eluted with a retention time of 7 min (radiochemical purity >98% and radiochemical yield: 97% decay corrected (reference to gallium-68 measured at the start of the reaction)). Additionally, $^{68}$Ga-Galuminox was also analyzed by radio-TLC (methanol (v/v 0.1% TFA)/water (v/v 0.1% TFA) in a ratio of 9:1 ($R_f$=0.53) using silica gel plates. The radiotracer was characterized by spiking an unlabeled analytically characterized sample of Galuminox (10 μg) with the $^{68}$Ga-Galuminox, using UV and radio-detectors. Finally, the purified radiolabeled fraction was diluted into sterile saline containing 2% ethanol (pH 7) and deployed for micro-PET imaging.

Detection of ROS Using Galuminox In Vitro Fluorescence Assay

Fluorescence assays were performed in phosphate buffer saline (PBS, lx, pH 7.2). Reagents were prepared and stored at 4° C. Catalytic enzymes were diluted using commercial buffers and stored as per manufacturer instructions. Final concentrations for Galuminox, glucose, glucose oxidase, xanthine, xanthine oxidase (XO), superoxide dismutase (SOD), catalase (CAT), Linsidomine (SIN-1 chloride), and 2,4-carboxyphenyl-4,4-5,5-tetramethyl-imidazoline-1-oxyl-3-oxide (CPTIO) are listed in Table 1 below. For fluorescence measurements, Galuminox was incubated with G-GOx /X-XO/SIN-1 either in absence or presence of SOD/CAT/CPTIO for 15 min at 37° C. All measurements of fluorescence were performed in triplicates, using a Corning 96-well (12 columns×8 rows) plate with a final volume of 200 μl per well. Data were collected using Varian Cary Eclipse Fluorescence Spectrophotometer (Plate reader), normalized to fluorescence of buffers without Galuminox, the fluorescence output was determined in arbitrary units, converted into % intensity, and plotted using Prism—GraphPad.

TABLE 1

Reagent concentrations used for fluorescence assay for detection of oxidation species with Galuminox.

| Reagents | Final Concentration | Source |
|---|---|---|
| Galuminox | 20 μM | |
| Glucose (G) | 50 μM | Sigma-Aldrich |
| Glucose oxidase (GOx) | 1 U/mL | Bioworld |
| Xanthine (X) | 200 μL/mL | Sigma-Aldrich |

TABLE 1-continued

Reagent concentrations used for fluorescence assay for detection of oxidation species with Galuminox.

| Reagents | Final Concentration | Source |
|---|---|---|
| Xanthine oxidase (XO) | 200 μL/mL | Sigma-Aldrich |
| Superoxide dismutase (SOD) | 600 U | Sigma-Aldrich |
| Catalase (CAT) | 25 μL/mL | Abcam |
| 3-Morpholinylsydnoneimine chloride (SIN-1) | 7.25 mM | Tocris |
| 2-(4-Carboxyphenyl)-4,4,5,5-tetramethylimidazoline-1-oxyl-3-oxide potassium salt (CPTIO) | 2.62 μM | Alfa Aesar |

Bioassays

Cell Culture

Human alveolar basal epithelial (A549) adenocarcinoma cells were grown in Dulbecco's Modified Eagle Medium (DMEM) supplemented with 1-glutamine (2 mM), penicillin/streptomycin (200 IU.) and heat-inactivated fetal calf serum (10%). The cells were grown at 37° C. under a 5% $CO_2$ atmosphere.

A549 Cells Expressing Mt-Keima mt-Keima has been described previously (N. Sun, et al. A fluorescence-based imaging method to measure in vitro and in vivo mitophagy using mt-Keima. Nat. Protoc., 12 (2017), pp. 1576-1587.). A modified mt-Keima cDNA was generated from the mt-Keima open reading frame encoded within pCHAC-mt-mKeima (Addgene, Waterman Mass.) by PCR amplification with primers that include an extra N-terminal MT-COX3 leader peptide to further enhance localization of Keima protein to mitochondria. The resulting mt-Keima cDNA PCR product was then subcloned into multiclonal site (5'Xba1, 3' EcoR1) of the lentiviral vector backbone Ex-EGFP-LV105 (Genecopia, Rockville, MD), which results in the deactivation of EGFP expression to create Ex-mt-Keima. Thereafter, Ex-mt-Keima lentiviral vector was packaged into lentiviral particles (Genecopia) and transfected into A549 cells (ATCC, Manassas Va.) at a 10: 1 multiplicity of infection under puromycin selection (Sigma, St Louis Mo.) treatment at 2 μg/ml.

Fluorescence Imaging Studies

Live cell fluorescence imaging studies were performed at Washington University Center for Cellular Imaging (WUCCI). For imaging studies, A549 cells or their mt-Keima transfected counterparts were plated onto borosilicate 8-well chambered coverglass (Labtek) and allowed to grow to approximately 70% confluence at 37° C. under 5% $CO_2$ atmosphere in the culture media (200 μL) and treated with LPS (1 μg/mL) for 24 h. Following LPS treatments, all wells were rinsed with fresh media. For evaluating impact of ROS on uptake profiles of the metalloprobe, cells were first incubated with mitoSOX (0.5 μM) at 37° C. for 15 min, then wells were rinsed with PBS (3×200 μL), and fresh media (200 μL) was added, followed by incubation with either Galuminox (20 μM) or media alone at 37° C. for 1 h, while maintaining continuous influx of 5% $CO_2$. However, for tracking of intracellular localization of the probe, following LPS treatments for 24 h, A549 cells were incubated simultaneously with either Galuminox (20 μM) and lysotracker Red (1 μM) or media alone at 37° C. for 1 h under continuous influx of 5% $CO_2$. Similarly, following treatments with LPS, mt-Keima transfected A549 cells were also incubated simultaneously with either Galuminox (20 μM) or media alone at 37° C. for 1 h under continuous influx of 5% $CO_2$. Cellular accumulation studies were performed by using an inverted Nikon A1Rsi laser scanning confocal microscope using either a 20× dry or 60× oil objective lens (Nikon Instruments Inc., NY, USA). 405, 514 and 640 nm lasers were used for the detection of Galuminox, MitoSOX and Lysotracker deep red, respectively. Throughout the data acquisition process, cells were maintained at 37° C. with 5% $CO_2$, controlled by a Tokai Hit stage-top incubation system (Shizuoka, Japan). Acquisition was performed using Nikon NIS-Elements software (Nikon Instruments Inc., NY, USA.). Images were processed and analyzed using the ImageJ software package (NIH). Cellular uptake of Galuminox was then quantified (wherein corrected total cellular fluorescence (CTCF)=integrated density-(area of selected cell×mean fluorescence of background readings) using protocols described elsewhere (B. Jakic, M. Buszko, G. Cappellano, G. Wick. Elevated sodium leads to the increased expression of HSP60 and induces apoptosis in HUVECs. PloS One, 12 (2017), Article e0179383.). The quantitative analysis for colocalized fluorescence signal within the merged channel was performed using EzColocalization, an open source plugin to ImageJ that enables quantification of colocalized signals from 2 or more channels in microscopy images. For analysis, ROIs were drawn on cells of both channels, scatter plots were obtained, and Pearson's Correlation Coefficients (PCC) were determined as described previously (K. W. Dunn, M. M. Kamocka, J. H. McDonald. A practical guide to evaluating colocalization in biological microscopy. Am. J. Physiol. Cell Physiol., 300 (2011), pp. C723-C742.).

For evaluation of therapeutic effects of drugs, such as Carvedilol (CAR), Dexrazoxane (DEX), and mitoTempo (MT) on either serum/glucose deprived media- or LPS-induced superoxide production, A549 cells were incubated with either LPS (1 μg/mL) or serum/glucose deprived (starvation) media for 24 h, and thereafter incubated with Carvedilol, Dexrazoxane, and mitoTempo 24 h at 37° C. Next day, media was removed from wells, cells were carefully rinsed with PBS (2×200 μL), fresh media (200 μL) was added, and cells were incubated with Galuminox (20 μM) at 37° C. for 60 min. For controls, untreated cells were incubated with Galuminox (20 μM) under identical conditions. Thereafter, fluorescence images were acquired, and cellular uptake was quantified as described above.

Quantification of ROS in Mouse Lung Cells

Quantitation of ROS post-LPS treatment was performed by using CellROX, a fluorogenic oxidative stress probe. CellROX is a cell-permeant dye and is weakly fluorescent in a reduced state. However, it exhibits bright green photostable fluorescence signal upon oxidation by reactive oxygen species (ROS) and subsequent binding to DNA, with absorption/emission maxima of 485/520 nm. Single cell lung suspensions were generated by cutting lung tissue into approximately 2 mm pieces and treatment with 0.5 mg/mL dispase (Sigma) and 5 units/mL of DNAse (Sigma) for 30 min at 37° C. and washed twice. Cell suspensions were filtered through a 70 micron filter and re-suspended at 200,000 cells per 500 μL of PBS and 5 μL of CellROX probe was added for 30 min at 37° C. Cells were then analyzed for CellROX uptake by a FACS-SCAN flow cytometer (BD Biosciences, San Jose, CA).

Preclinical PET/CT Imaging

All animal procedures were approved by the Washington University Animal Studies Committee. Imaging and biodistribution studies were performed in C57Bl6 mice (average weight, 24 g). Male mice (n=4) were treated either with LPS at a dose of 5 μg/g or vehicle (saline) 24 h prior to imaging/biodistribution studies. For these studies, mice were anesthetized with isoflurane (2.0%) via an induction chamber and maintained with a nose cone. After anesthetization, the mice were secured in a supine position and placed in an acrylic imaging tray. Following intravenous tail-vein administration of $^{68}$Ga-Galuminox (100 μL; 100 μCi; 2% ethanol in saline, 3.7 MBq), dynamic preclinical PET scans were performed over 60 min, using Inveon PET/CT scanner (Siemens Medical Solutions). PET data were stored in list mode, and reconstruction was performed using a 3D-OSEM method with detector efficiency, decay, dead time, attenuation, and scatter corrections applied. For anatomical visualization, PET images were also co-registered with CT images from an Inveon PET/CT scanner. ROIs were drawn over the lung, and standard uptake values (SUV) were calculated as the mean radioactivity per injected dose per animal weight.

Biodistribution Studies (Post Preclinical Imaging)

All animal procedures were approved by the Washington University Animal Studies Committee. Following microPET/CT imaging, mice (n=4) were euthanized by cervical dislocation. Blood samples were obtained by cardiac puncture, organs then harvested rapidly, and all tissue samples analyzed for γ-activity using Beckman Gamma 8000 counter. All samples were decay-corrected to the time the γ-counter was started. Standard samples were counted with the organs for each animal and represent 100 of the injected dose. An additional dose was diluted into milliQ water (100 mL) and aliquots (1 mL) were counted with each mouse. Data were quantified as the percentage injected dose (% ID) per gram of tissue (tissue kBq (injected kBq)$^{-1}$ (g tissue)$^{-1}$×100) in Table 2, shown below.

TABLE 2

Biodistribution data (% ID/g) for $^{68}$Ga-Galuminox at 60 min in mice (mean ± SEM, n = 4).

| | Control | | LPS | | |
|---|---|---|---|---|---|
| Organs | Mean | SEM | Mean | SEM | p-value |
| Blood | 2.821595 | 0.880175 | 3.960169 | 1.828668 | 0.405568 |
| Lung | 39.70327 | 19.30533 | 147.8875 | 25.83703 | 0.005529 |
| Liver | 6.138188 | 0.655342 | 10.45633 | 1.684508 | 0.033823 |
| Kidney | 13.0965 | 0.932392 | 3.048004 | 0.718104 | 0.000182 |
| Muscle | 1.084462 | 0.120034 | 0.294012 | 0.093178 | 0.001103 |
| Fat | 0.61172 | 0.22274 | 0.302115 | 0.034583 | 0.134625 |
| Heart | 2.380763 | 0.500028 | 1.072794 | 0.255039 | 0.027798 |
| Brain | 0.569331 | 0.093869 | 0.262796 | 0.09788 | 0.017379 |
| Bone | 1.001514 | 0.338047 | 2.138463 | 0.567722 | 0.052753 |
| Bladder | 162.956 | 79.28965 | 5.892614 | 3.962169 | 0.0751 |
| Intestine | 4.285932 | 0.914849 | 1.314352 | 0.456687 | 0.01588 |
| Colon | 0.861722 | 0.460285 | 0.292394 | 0.134587 | 0.157242 |

Lung Histology and Pulmonary Edema Studies

For wet to dry ratio the left lung mass was assessed before (wet) and after (dry) dehydration for 72 h at 65° C. To measure airway protein bronchoalveolar lavage (3×1.0 ml saline extractions) was assayed for total protein content by absorbance at 595 nm (μQuant-Biotek) using a Bradford kit Protein Assay (BioRad) and bovine serum albumin as a standard (BSA), (Sigma). For histology, lung grafts were harvested, inflation fixed in formaldehyde, embedded in paraffin, sectioned, and stained with hematoxylin and eosin.

Statistical Analysis

Statistical analysis was performed using unpaired Student's t-test using GraphPad Prism version 6.0 (GraphPad Software, San Diego, CA) or Excel 2016 (Microsoft, Redmond, WA). For all comparisons, $p<0.05$ was considered statistically significant.

Example 2

For conceptualizing radiotracers, ROS-sensitive fluorescent probes such as DHE (dihydroethidium), mitoSOX, and 5-(and 6)-chloromethyl-2',7'-dichlorohydrofluorescein diacetate (CM-$H_2$DCFDA) are shown with Galuminox (FIG. 1).

Example 3

Figure 2A:
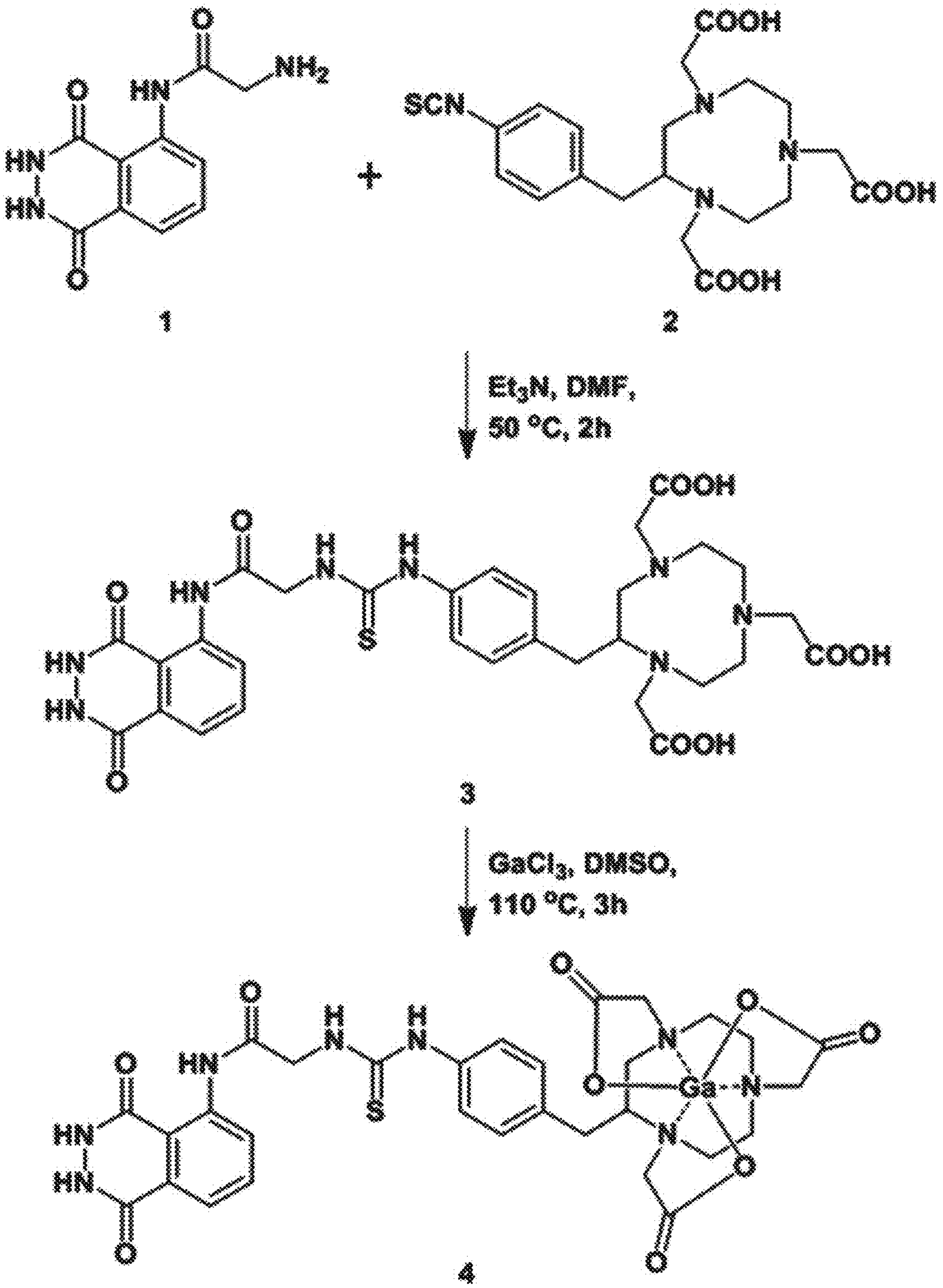
FIG. 2A depicts the scheme for the chemical synthesis of Galuminox.

Ga-LG-NOTA (which is now described as Galuminox (see FIG. 1 and FIG. 2A, (4)), is a metalloprobe for the detection of total ROS. Galuminox was synthesized through reaction between LG-NOTA, the precursor ligand and $GaCl_3$ dissolved in dimethylsulfoxide (FIG. 2A), purified, and analytically characterized. Proton NMR of Galuminox demonstrated a symmetrical coordination of the central gallium to the coordination core ($N_3O_3$) of the precursor ligand. Galuminox, when solubilized in PBS with 1.0% ethanol and excited with a 405 nm laser, exhibited a broad emission peak between 450 and 540 nm with a maxima of 490 nm.

Figure 2B:
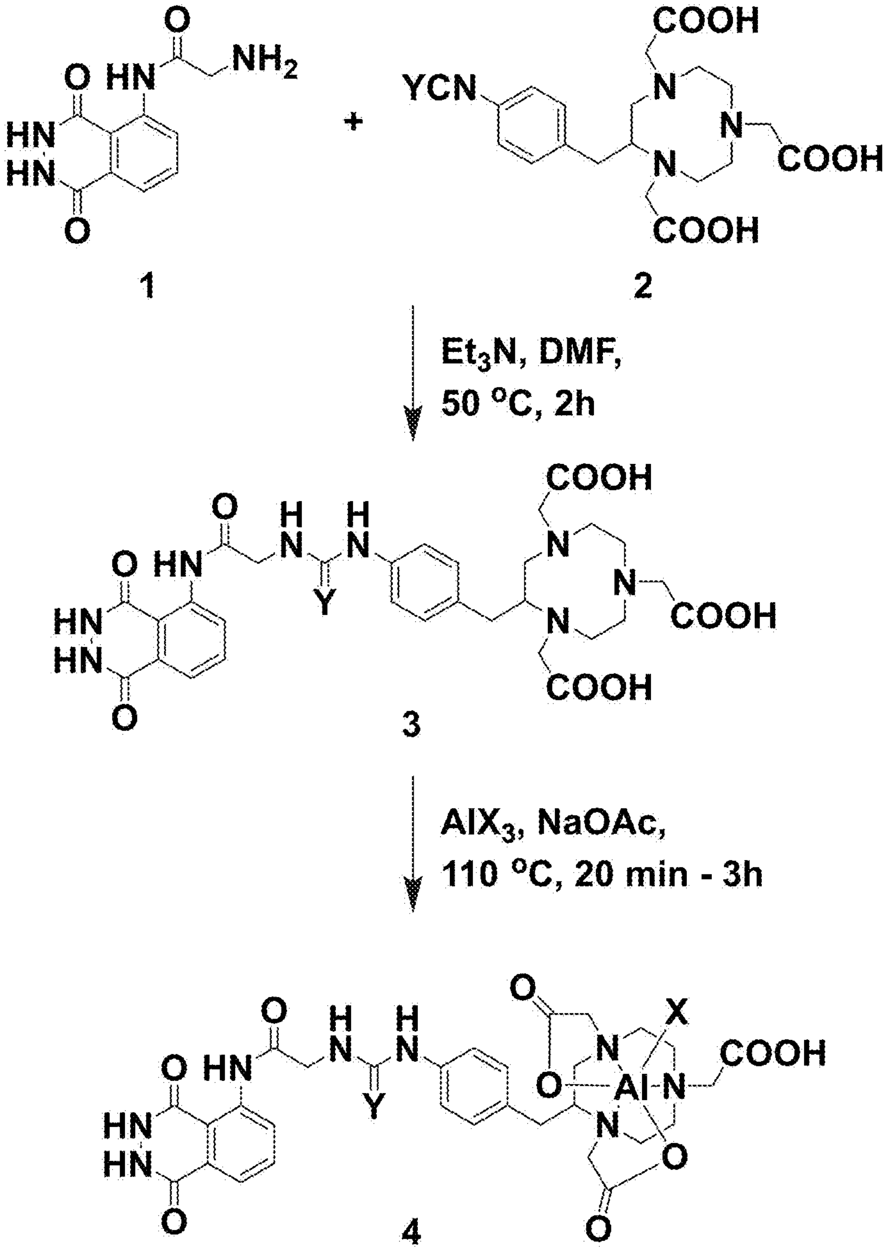
FIG. 2B depicts the general scheme for the chemical synthesis of imaging agents containing Al$^{18}$F and Al$^{123/131}$I as the radiolabel component.
Figure 2C:
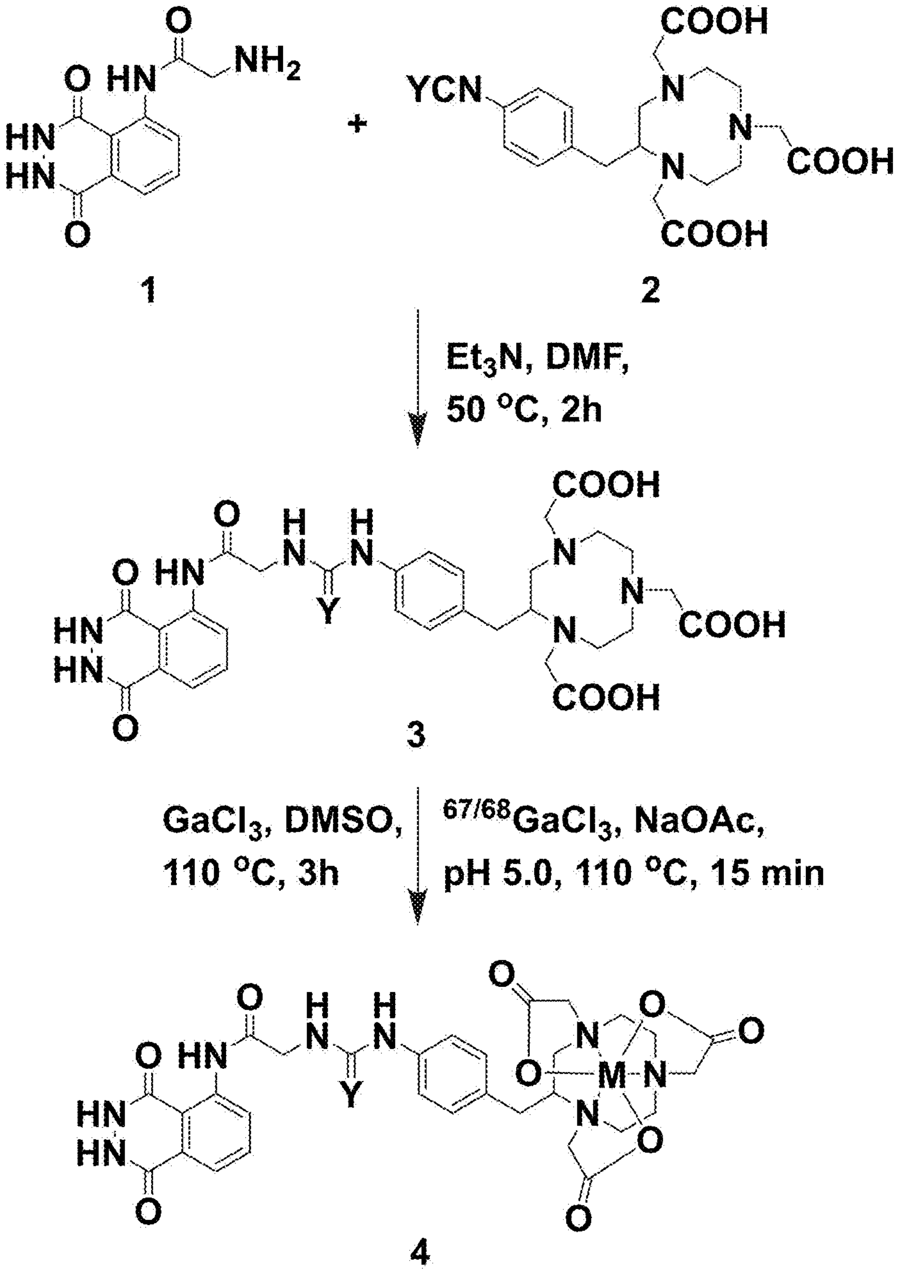
FIG. 2C depicts the general scheme for the chemical synthesis of Galuminox-related imaging agents containing $^{67/68}$Ga as the radiolabel component.
Figure 2D:
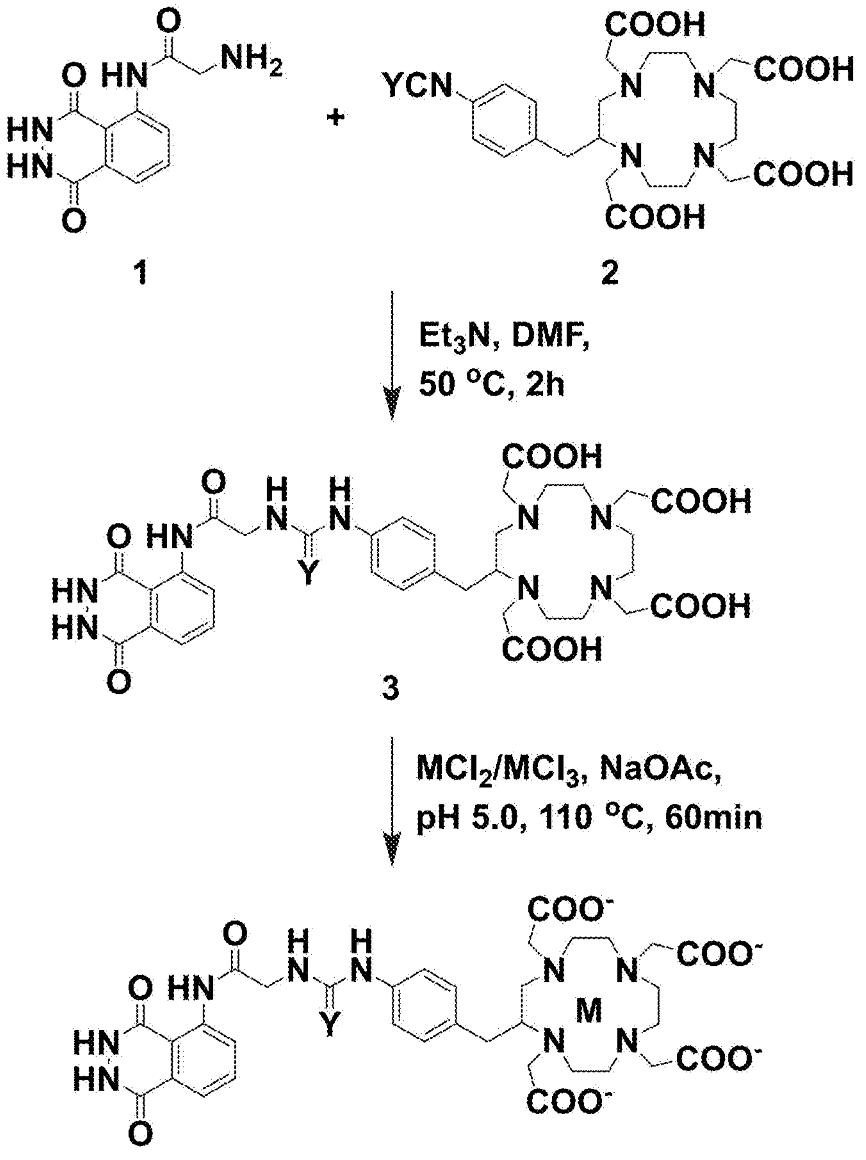
FIG. 2D depicts the general scheme for the chemical synthesis of imaging agents containing a 1,4,7,10-tetraazacyclododecane-1,4,7,10-tetraacetic acid (DOTA) derivative as the chelator and $^{67/68}$Ga, $^{64}$Cu, or $^{111}$In as the radiolabel component.
Figure 2E:
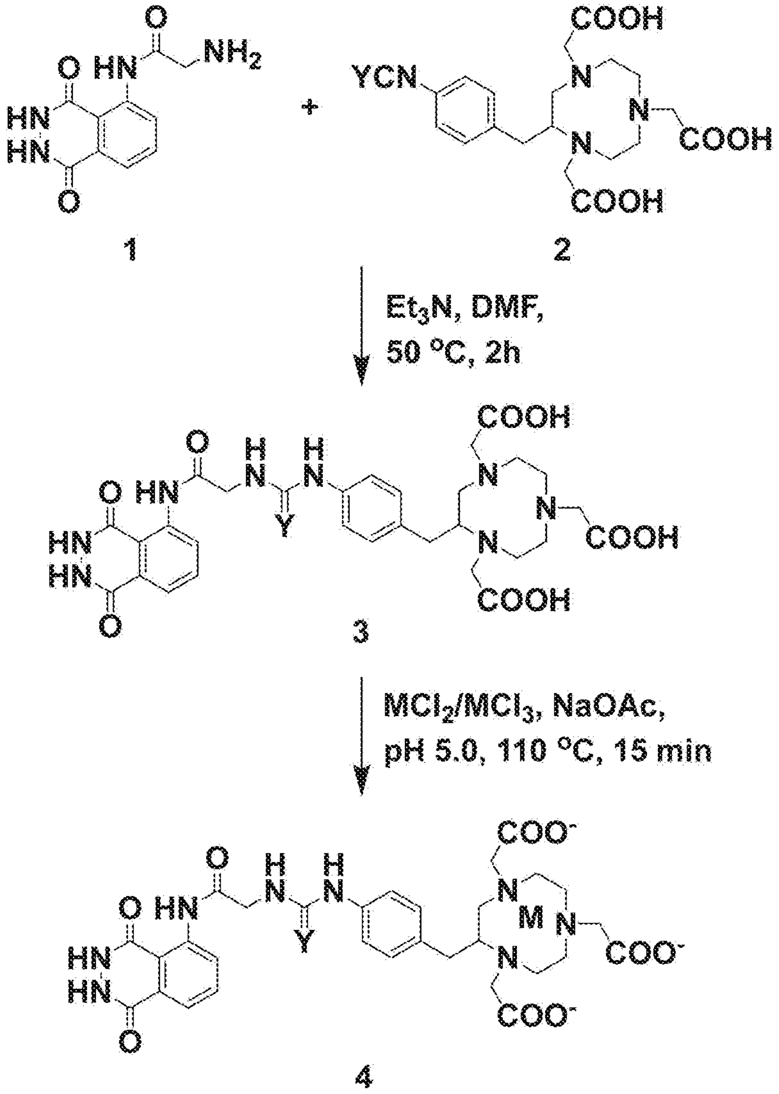
FIG. 2E depicts the general scheme for the chemical synthesis of imaging agents containing a 2-[4,7-Bis(carboxymethyl)-1,4,7-triazonan-1-yl]acetic acid (NOTA) derivatives as the chelator and $^{67/68}$Ga, $^{64}$Cu, or $^{111}$In as the radiolabel component.

Other general synthesis schemes are shown for using $AlF^{18}$ and $AlI^{123/131}$ as the radiolabel component (FIG. 2B), $Ga^{67/68}$ as the radiolabel component (FIG. 2C), 1,4,7,10-tetraazacyclododecane-1,4,7,10-tetraacetic acid (DOTA) derivatives as the chelator and $^{67/68}$Ga, $^{64}$Cu, or $^{111}$In as the radiolabel component (FIG. 2D), and 2-[4,7-Bis(carboxymethyl)-1,4,7-triazonan-1-yl]acetic acid (NOTA) derivatives as the chelator and $^{67/68}$Ga, $^{64}$Cu, or $^{111}$In as the radiolabel component (FIG. 2E).

Example 4

Integrated ROS comprise chemically reactive products of molecular oxygen ($O_2$) including the one-electron reduction product of molecular oxygen: superoxide ($O_2^-$). The superoxide can originate from numerous sources in vivo, including the mitochondrial electron transport chain and NADPH oxidase(s), which are activated under conditions of inflammation, ischemia, and tissue injury. Superoxide has also been shown to regulate distinct signaling cascades with specific molecular targets. Therefore, the ability to detect elevated ROS in patients could provide a better understanding of relationships between ROS, tissue injury, and disease staging. Furthermore, the ability to selectively identify specific ROS species may reveal critical information on signaling cascade that promote inflammation. Collectively, ROS processes involve formation of different reactive oxygen species.

To measure ROS production, a large number of methods have been developed and are based upon detection by colorimetry, chemiluminescence, and fluorescence, depending on the probe used. While xanthine-xanthine oxidase (X-XO) and SIN-1 have been used for production of superoxide and nitric oxide (wherein the combination produces peroxynitrite), respectively, the glucose-glucose oxidase (G-GO) system has been deployed for production of hydrogen peroxide. Employing concentrations of Galuminox and X-XO, SIN-1, and G-GO in vitro conditions (Table 1), the ability of Galuminox to detect different reactive oxygen species at 37° C. in PBS under physiological conditions (pH 7.2) was evaluated and fluorescence output was compared to that of untreated metalloprobe as a control using a fluorescence plate reader assay.

Figure 3A:
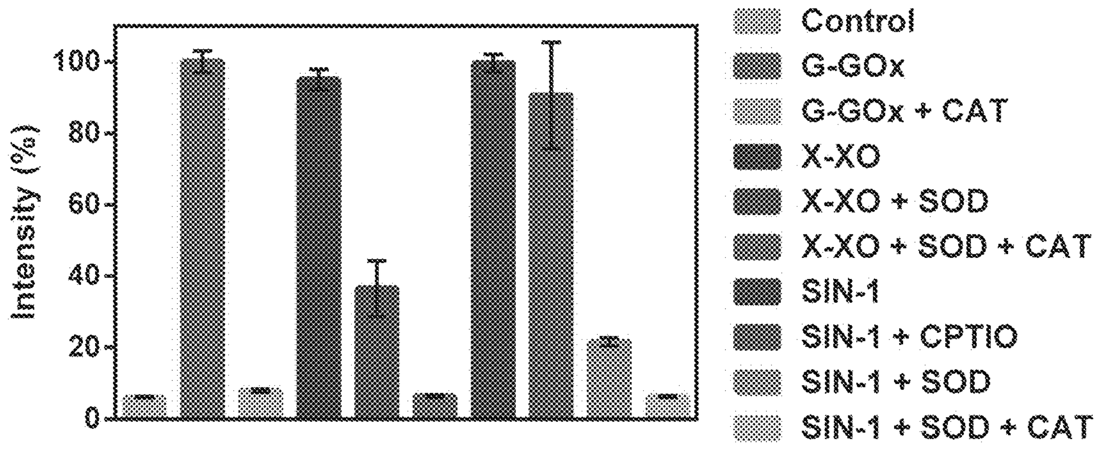
FIG. 3A depicts evaluation of Galuminox for detection of reactive oxygen species in vitro. Data are shown as the percent of hydrogen peroxide contribution to the fluorescence signal of Galuminox. Labels from top to bottom correspond to columns from left to right. Abbreviations: G: Glucose; GOx: Glucose oxidase; X: Xanthine; XO: Xanthine oxidase; SOD: Superoxide Dismutase; CAT: Catalase; SIN-1: 3-Morpholinylsydnoneimine chloride (SIN-1); and CPTIO: 2-(4-Carboxyphenyl)-4,4,5,5-tetramethylimidazoline-1-oxyl-3-oxide.

Two different biochemical systems were deployed for production of superoxide. While catalysis of xanthine by bovine-derived xanthine oxidase produces superoxide and the down-stream product, hydrogen peroxide, SIN-1 chloride in aqueous conditions through spontaneous decomposition produces superoxide and nitric oxide thus resulting in production of peroxynitrite. The former combination was also incubated with superoxide dismutase to analyze contribution of the superoxide to the fluorescence signal. The catalysis of xanthine by bovine-derived xanthine oxidase in combination of superoxide-dismutase and catalase demonstrated percent of hydrogen peroxide contribution to the fluorescence signal of Galuminox (FIG. 3A). The samples using SIN-1 chloride were also incubated with 2,4-carboxyphenyl-4,4-5,5-tetramethyl-imidazoline-1-oxyl-3-oxide (CPTIO), an effective nitric oxide scavenger, to analyze contribution of superoxide to the fluorescence signal of Galuminox under nearly physiological conditions. Finally, the catalysis of glucose with glucose oxidase produces hydrogen peroxide, and catalase converts hydrogen peroxide to water and carbon dioxide. Thus the biochemical system replicate enzyme catalyzed production of hydrogen peroxide under physiological conditions, while presenting opportunities to evaluate reactivity of Galuminox with hydrogen peroxide. Therefore, Galuminox fluorescence in a biochemical system comprising glucose/glucose oxidase/catalase also indicate specificity of the probe towards hydrogen peroxide (FIG. 3A).

Figure 3B:
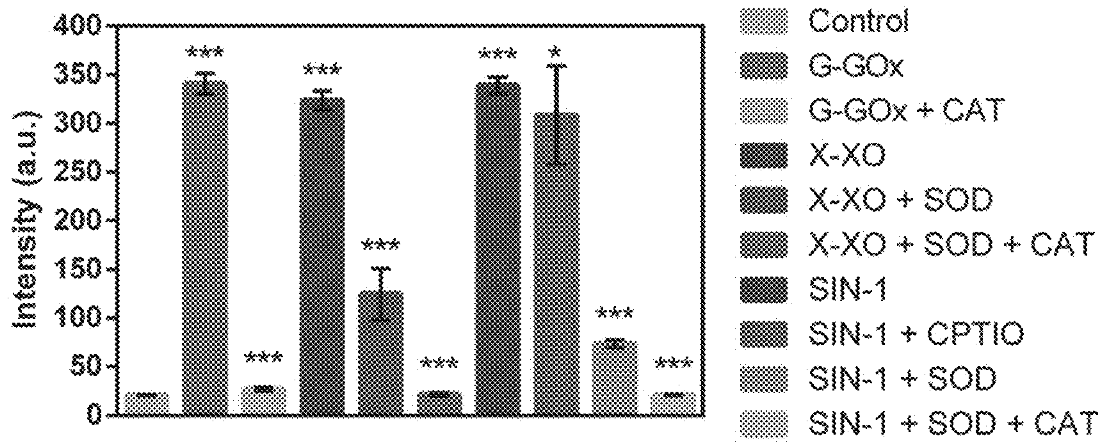
FIG. 3B depicts evaluation of Galuminox for detection of reactive oxygen species in vitro in arbitrary units. Data are shown as mean fluorescence intensity (arbitrary units) ±SEM, where ***$p<0.001$ and *$p<0.4$ are determined by an unpaired student t-test. Labels from top to bottom correspond to columns from left to right. Abbreviations are the same as in FIG. 3A.

The results in FIG. 3B show the intensity in arbitrary units. Galuminox showed ability to detect superoxide generated through either xanthine oxidase metabolism of xanthine or by thermal decomposition of SIN-1 in the presence of CPTIO. Under both conditions, oxidation of the probe was neutralized by the addition of superoxide dismutase (SOD) (FIG. 3B). Furthermore, the metalloprobe showed ability to detect hydrogen peroxide produced during glucose oxidase catalyzed oxidation of glucose to gluconate. Under these conditions, the oxidation of the probe was mitigated in presence of catalase (CAT), which converts the hydrogen peroxide into carbon dioxide and water, thus indicating specificity of the probe to detect hydrogen peroxide (FIG. 3B). Overall, the combined data indicate that Galuminox detects both superoxide and its downstream product, hydrogen peroxide.

Example 5

It has been shown that radiolabeled metalloprobes offer sensitive tools for evaluating quantitative accumulation of chemical entities within pooled cell populations. Although beneficial in translational nuclear imaging, this method precludes interrogation of pharmacological effects at a single cell level, within the same segment of cell population. Compared with radiotracer bioassays, fluorescence imaging offers a cost-efficient ionizing-radiation free technique to assess accumulation of metalloprobes at a single cell level, while beneficial in determining their intracellular localization under live cell conditions.

Figure 4A:
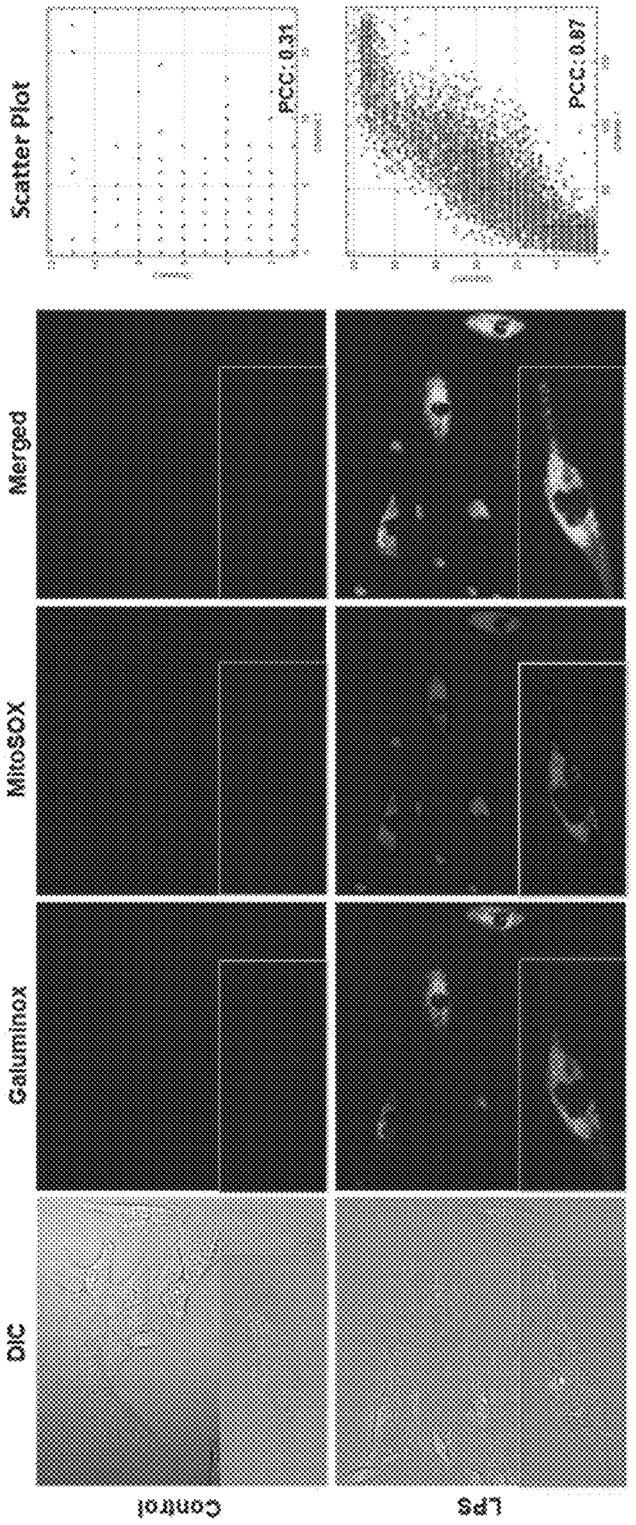
FIG. 4A depicts cellular accumulation of Galuminox in LPS-treated A549 cells and correlation with mitoSOX. Images were acquired using a 20× objective (all panels represent same magnification) in live human adenocarcinoma alveolar basal epithelial (A549) cells following incubation either in absence (control) or presence of LPS (1 μg/mL) for 24 h. Following treatment with LPS, A549 cells were incubated with Galuminox (20 μM) at 37° C. for 60 min in the presence of MitoSOX (25 nM). Shown is an uptake of Galuminox in A549 cells in reference to mitoSOX (ROS probe) under identical conditions. INSET (All Panels): Single Cell Image (Magnification: 60×). Right: Scatter plots show relationships of spatial overlaps Galuminox and mitoSox pixel intensities in A549 cells and their quantitative correlations using Pearson correlation coefficients (PCC).

Lipopolysaccharide (LPS), also commonly known as endotoxin, is the major constituent of the outer cell wall of Gram-negative bacteria and is potent driver of ALI in septic patients. LPS is detected by toll-like receptor 4 (TLR4), a broadly expressed pattern recognition receptor found both on leukocytes and nonhematopoietic cells. TLR4 engagement triggers the generation of mitochondrial superoxide from electron transport complex I, which in turn promotes bacterial killing. To this end, ROS production was simultaneously assessed with the mitochondrial-superoxide probe MitoSOX and Galuminox in the human lung alveolar epithelial carcinoma cell line A549 following LPS stimulation (FIG. 4A). When compared to untreated A549 control cells, LPS stimulation induced both higher fluorescence of MitoSOX and Galuminox, while exhibiting a distinct pattern of probe co-localization, suggesting that Galuminox was taken up by superoxide-producing mitochondria (FIG. 4A).

Figure 4B:
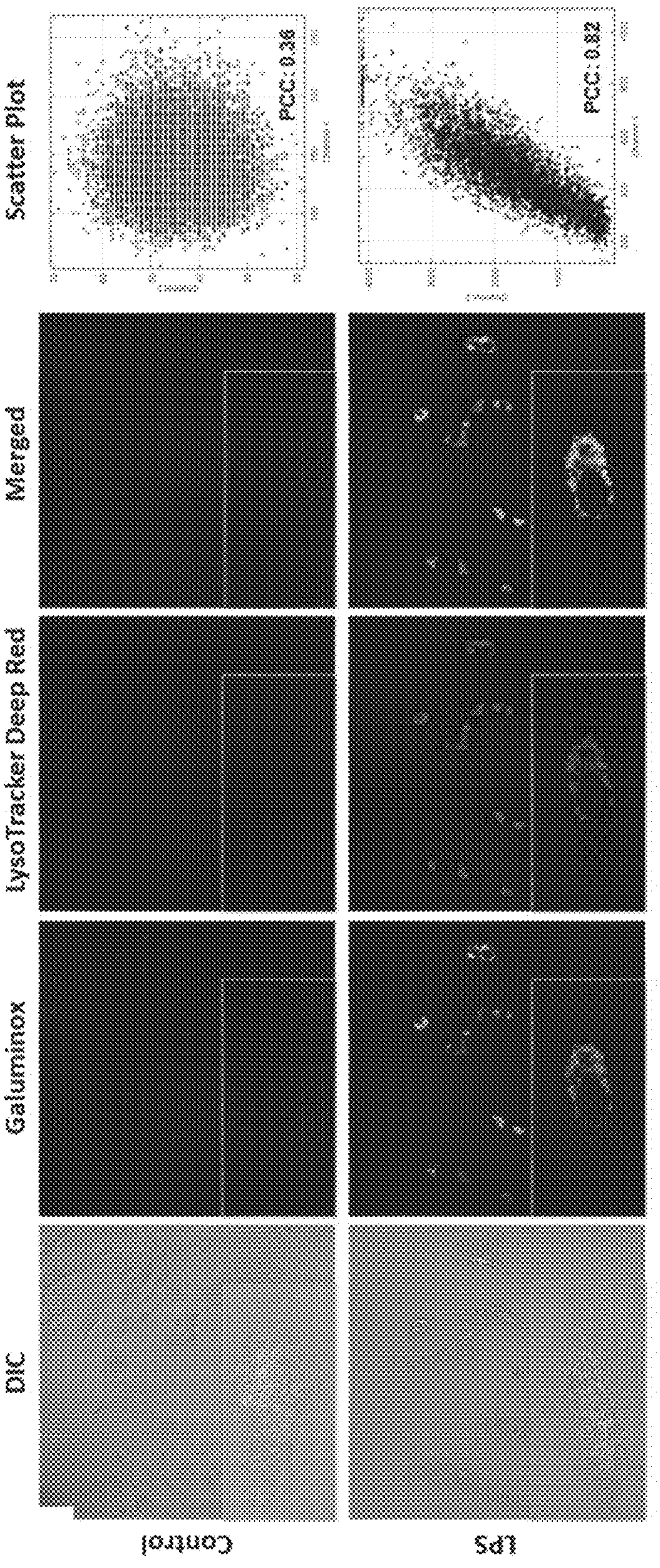
FIG. 4B depicts cellular accumulation of Galuminox in LPS-treated A549 cells and correlation with Lysotracker. Images were acquired using a 20× objective (all panels represent same magnification) in live human adenocarcinoma alveolar basal epithelial (A549) cells following incubation either in absence (control) or presence of LPS (1 μg/mL) for 24 h. Following treatment with LPS, A549 cells were incubated with Galuminox (20 μM) at 37° C. for 60 min in the presence of Lysotracker (1 μM). Shown is an uptake of Galuminox in A549 cells in reference to lysotracker (lysosome marker) under identical conditions. INSET (All Panels): Single Cell Image (Magnification: 60×). Right: Scatter plots show relationships of spatial overlaps Galuminox and Lysotracker pixel intensities in A549 cells and their quantitative correlations using Pearson correlation coefficients (PCC).

It was previously known that TLR4 engagement also induces the co-localization of ROS-generating mitochondria to low pH intracellular compartments such as phagolysosomes and also leads to stimulation of autophagy in airway epithelial cells, which in turn can promote ROS production within lysosomes. Thus, the next experiment was to attempt to observe intracellular Galuminox activity within lysosomes. LPS stimulated A549 cells were co-stained with Galuminox and the pH sensitive fluorescent probe lysotracker (FIG. 4B). Galuminox demonstrated marked co-localization with lysotracker stained vesicles in LPS-treated A549 cells, indicating that Galuminox detected ROS production also within lysosomes.

Figure 4C:
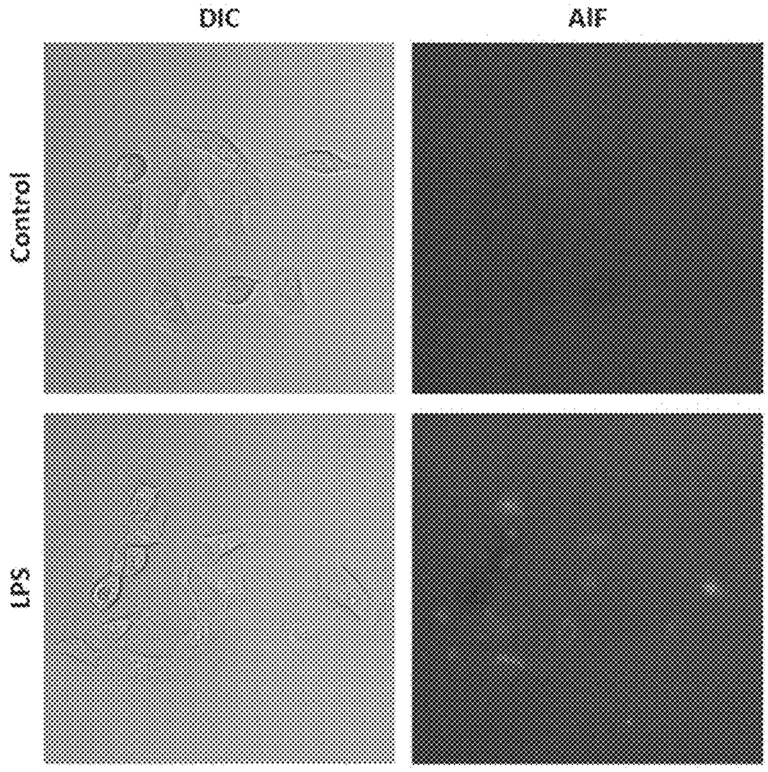
FIG. 4C depicts cellular accumulation of an aluminum fluoride counterpart of Galuminox (AlF) in LPS-treated A549 cells compared to control. DIC shows the outline of cells, and AlF shows the fluorescent signal of the probe.
Figure 4D:
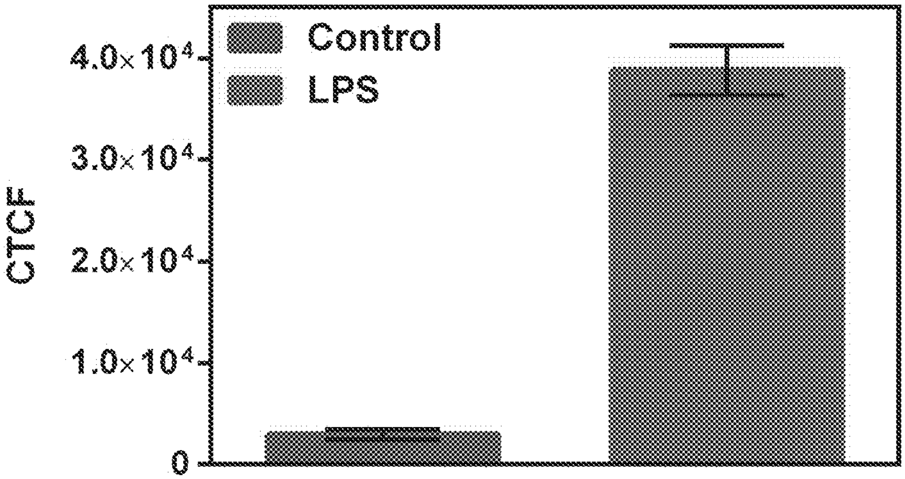
FIG. 4D depicts the Corrected Total Cell Fluorescence (CTCF) of the fluorescent signal of the data represented in FIG. 3D. The labels from top to bottom correspond to the columns from left to right.

An aluminum fluoride Galuminox counterpart (see synthesis in FIG. 2B) was also used on LPS and control treated cells (FIG. 4C), and the quantified fluorescent signal was much higher in LPS treated cells (FIG. 4D).

Example 6

Figure 5A:
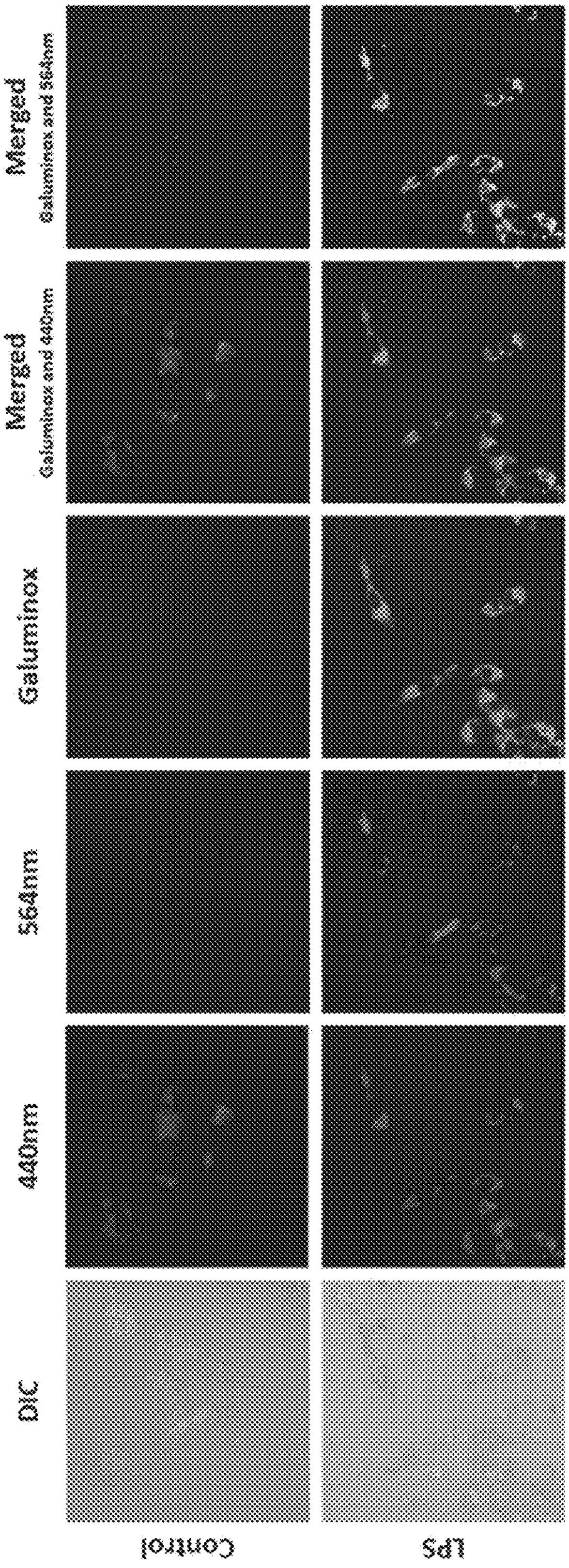
FIG. 5A depicts cellular accumulation of Galuminox in LPS-treated mt-Keima transfected A549 cells. Images were acquired using a 60× objective in live mt-Keima transfected A549 cells following incubation either in absence (control) or presence of LPS (1 μg/mL) for 24 h. Following treatment with LPS, mt-Keima transfected A549 cells were incubated with Galuminox (20 μM) at 37° C. for 60 min. Top Panel: Control; Lower Panel: LPS treated. Galuminox preferentially detects mitochondrial ROS (see merged image of Galuminox with Keima 440 nm) in the cytoplasm.
Figure 5B:
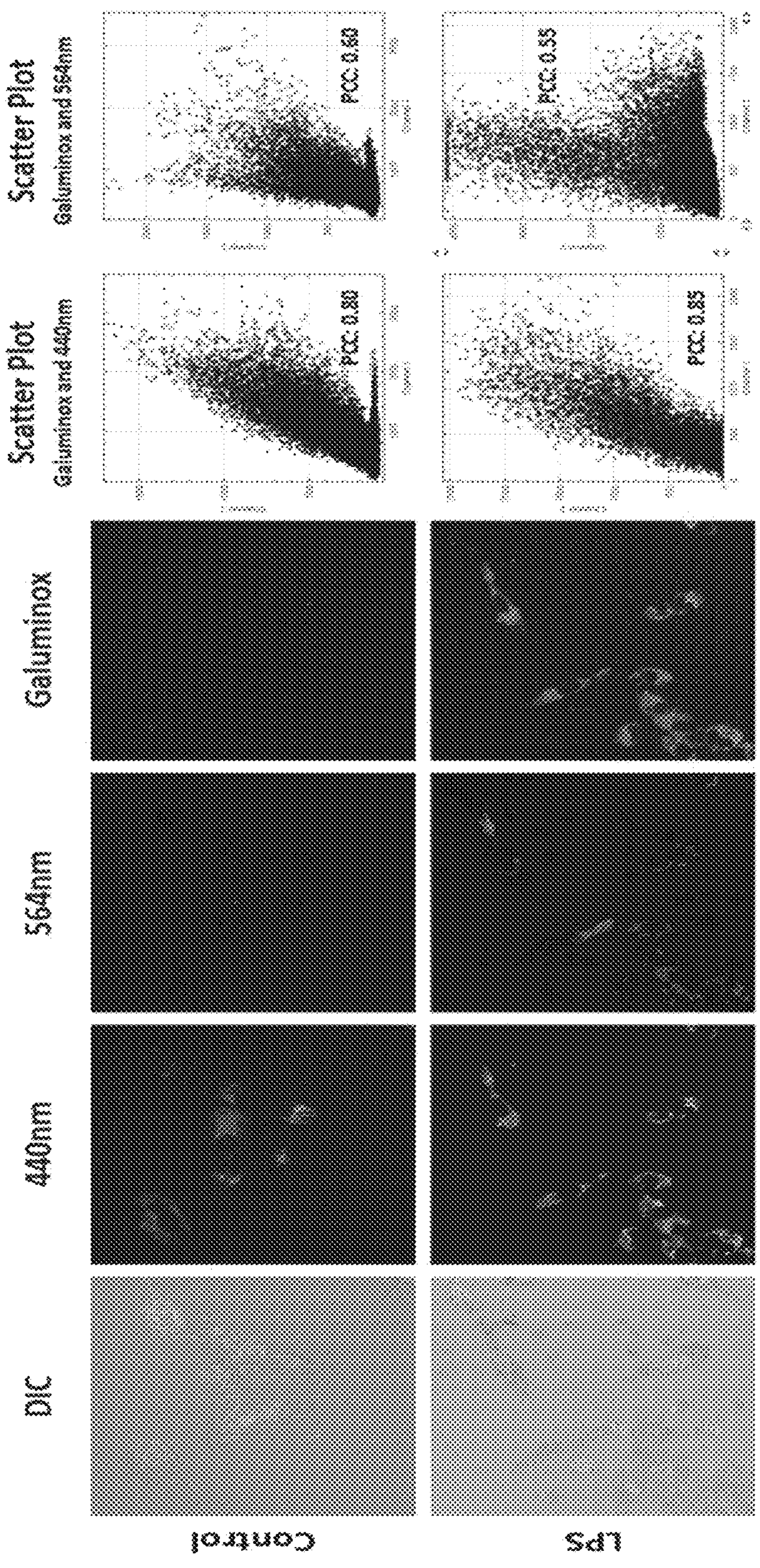
FIG. 5B depicts cellular accumulation of Galuminox in LPS-treated mt-Keima transfected A549 cells with additional scatter plots. Images were acquired using a 60× objective in live mt-Keima transfected A549 cells following incubation either in absence (control) or presence of LPS (1 μg/mL) for 24 h. Following treatment with LPS, mt-Keima transfected A549 cells were incubated with Galuminox (20 μM) at 37° C. for 60 min. Top Panel: Control; Lower Panel: LPS treated. Right: Scatter plots show relationships of spatial overlaps of Galuminox and mt-Keima 440 nm or mt-Keima 564 nm pixel intensities and their quantitative correlations using Pearson correlation coefficients (PCC). Note: Galuminox preferentially detects mitochondrial ROS (see also scatter plot with Pearson correlation coefficients).

Mitochondria can produce ROS either within the cytoplasm or during autophagic removal and eventual sequestration within lysosomes—a process commonly referred to as mitophagy. This aspect raised the possibility that Galuminox was measuring mitochondria ROS in one or both compartments. To answer this question explicitly, A549 cells were utilized that express mitochondrial targeted Keima (mt-Keima), a coral-derived acid-stable fluorescent protein that emits different-colored signals under acidic and neutral conditions. mt-Keima excitation peak shifts from 440 nm (under conditions of physiological pH in cytosol) to 586 nm (Lysosome pH: 4.0). Following LPS treatment of A549 cells that express mt-Keima, Galuminox showed a higher correlation with mt-Keima in the cytoplasm (440 nm, PCC: 0.86; FIG. 5B) than lysosome (564 nm; PCC: 0.55; FIG. 5B) for detection of ROS (FIG. 5A). Given that it was also observed that Galuminox co-localizes with MitoSOX-stained mitochondria (FIG. 4A), these data collectively suggested that Galuminox largely measures ROS production by mitochondria in the cytoplasm.

Example 7

Figure 6:
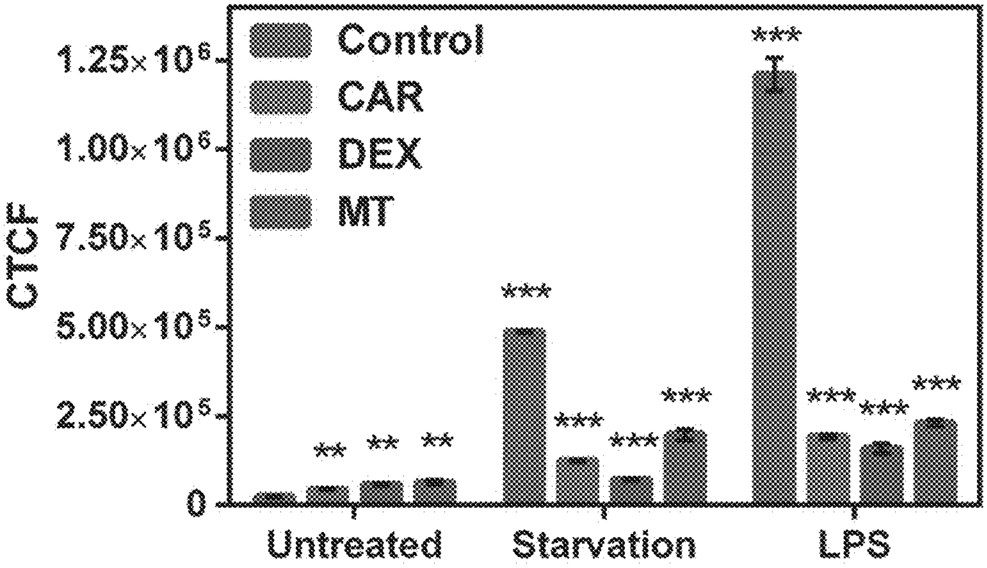
FIG. 6 depicts cellular accumulation of Galuminox either in serum and glucose deprived- or LPS-treated treated A549 cells either in presence or absence of Carvedilol (CAR), Dexrazoxane (DEX), and MitoTEMPO (MTT). Images were acquired using a 20× objective (all panels represent same magnification) in live human adenocarcinoma alveolar basal epithelial A549 cells. While A549 control cells were plated under normal conditions, both serum- and glucose-deprived (Starvation), and LPS treated cells were allowed to recover in presence of Carvedilol (CAR), Dexrazoxane (DEX), and MitoTEMPO (MTT) for 48 h, and treated with Galuminox (20 μM) for 60 min, cell uptake was evaluated via live-cell imaging, and quantified. Corrected Total Cell Fluorescence (CTCF)=Integrated Density-(Area of selected cell×Mean fluorescence of background readings); (mean±SEM), where *$p<0.001$ and $p<0.01$ are determined by an unpaired student t-test. For each treatment condition, the labels from top to bottom correspond to the columns from left to right.

It was next tested if mitigating mitochondrial oxidative stress through three different therapeutic strategies could be monitored by reductions in Galuminox activity. Carvedilol (CAR) is thought to reduce oxidative stress through inhibiting the mitochondrial exogenous nicotinamide adenine dinucleotide phosphate oxidase (NOX) activity. Additionally, when CAR is co-administered with doxorubicin, an anticancer drug, it reduces cell vacuolization in cardiomyocytes, preventing inhibition of mitochondrial respiration, thus mitigating doxorubicin induced reduction of $Ca^{2+}$ loading. Dexrazoxane (DEX) is an FDA approved drug for advanced breast cancer and functions by chelating free iron required for the catalytic function of mitochondrial NADH oxidase activity. Finally, Mito-Tempo (MT) is mitochondria-targeted antioxidant that functions as a superoxide dismutase mimetic and has been shown effective against experimental endotoxin-induced liver injury and induction of mitochondrial NADH oxidase complex I superoxide activity in response to nutrient-deprivation-induced autophagy. For investigating the ability of Galuminox to measure therapeutic mitigation of ROS activity, in the presence or absence of CAR, DEX or Mito-Tempo, A549 cells were treated with LPS or nutrient-deprived A549 cells (by serum and glucose withdrawal) to induce ROS. Twenty-four-hours (24 h)—post-LPS treatment or nutrient deprivation of A549 cells, Galuminox uptake was analyzed by live cell fluorescence imaging (FIG. 6). LPS-treated and nutrient deprived—A549 cells showed high retention of Galuminox in untreated (control) cultures. In contrast, however, probe uptake was significantly decreased in the presence of CAR, DEX, and Mito-Tempo when compared to control A549 cells. Some of these observations may also be explained by LPS-mediated mitochondrial depolarization or autophagic death, which can also lead to superoxide generation through the induction of mitochondrial intrinsic apoptosis. Taken together, these data showed Galuminox imaged ROS mitigating therapy in A549 cells.

Example 8

Figure 7A:
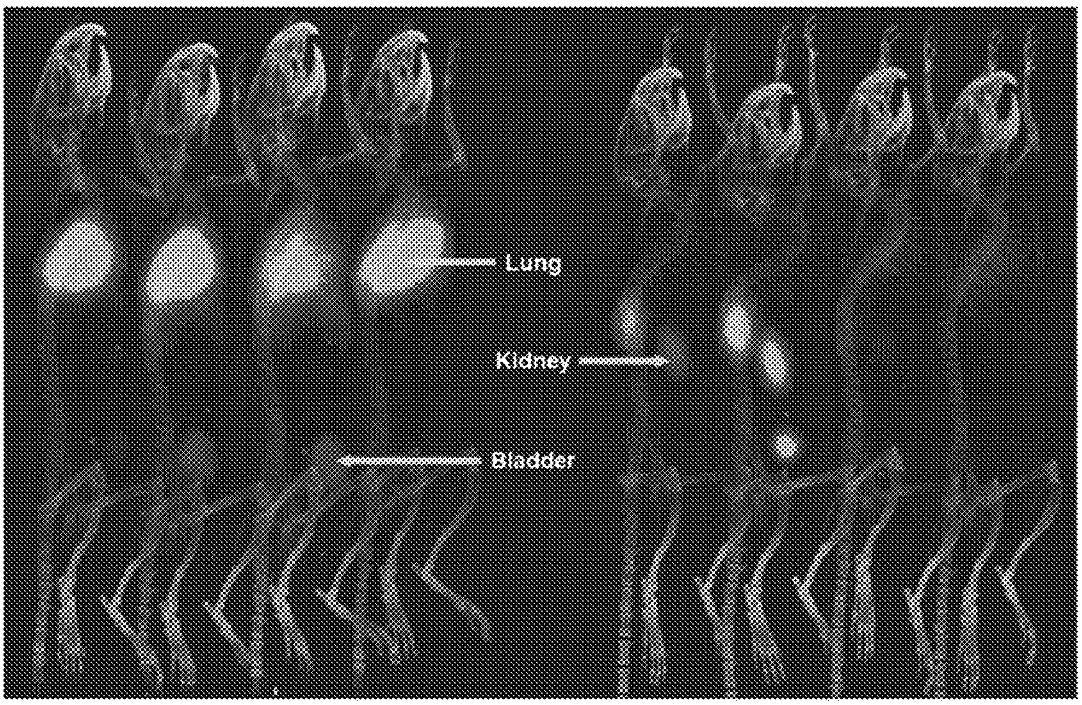
FIG. 7A depicts preclinical PET/CT Imaging. C57Bl6 mice (n=4) were injected with either LPS or saline intraperitoneally. Following treatments, $^{68}$Ga-Galuminox was injected via tail-vein into mice. Dynamic PET images were acquired from 0 min to 60 min post tail-vein injection. PET/CT images as shown are a summation frames from 45 to 60 min. Left Panel: LPS (5 μg/g, 24 h post treatment); Right Panel: Saline-treated mice.
Figure 7B:
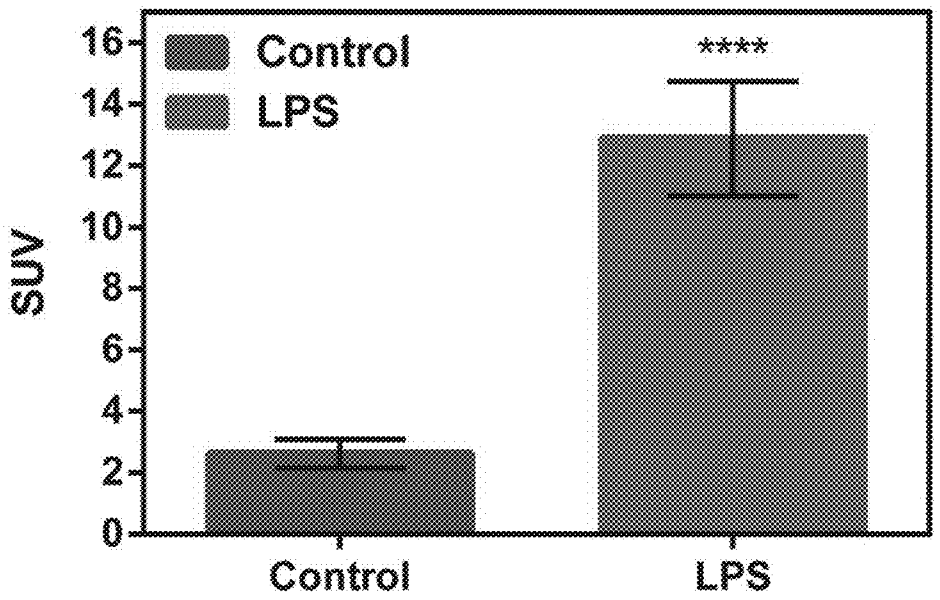
FIG. 7B depicts SUV analysis of $^{68}$Ga-Galuminox uptake. SUV analysis of $^{68}$Ga-Galuminox uptake (mean±SEM, where ****$p<0.0001$ is determined by an unpaired student t-test) in lungs of B16 mice (n=4) 24 h post either LPS- or saline treatments.
Figure 7C:
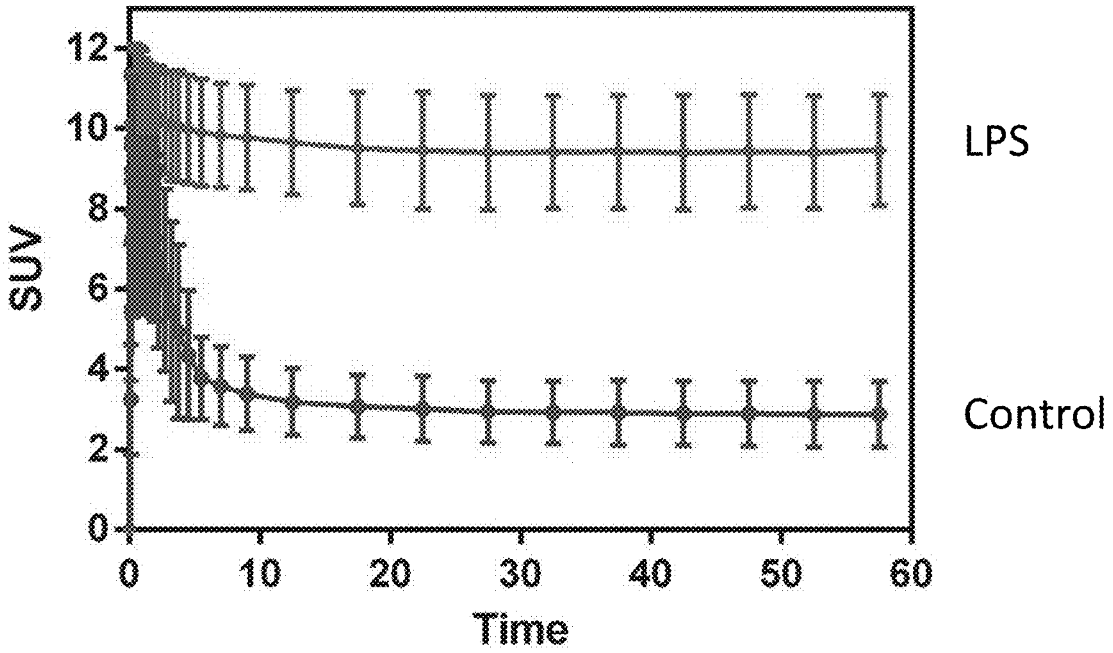
FIG. 7C depicts SUV Time-Activity Curve (TACs) of $^{68}$Ga-Galuminox uptake. SUV Time-Activity Curve (TACs) of $^{68}$Ga-Galuminox uptake in lungs of B16 mice 24 h post either LPS- or saline treatments indicating high and stable retention in lungs of LPS treated mice compared with their saline-treated counterparts.

For interrogating potential of Galuminox to serve as a ROS imaging probe in vivo, a well-established mouse model of LPS-mediated ALI was utilized. In order to accomplish this objective, the PET mimetic, $^{68}$Ga-Galuminox was prepared using a ligand exchange reaction. Preclinical PET/CT images at 1 h (summation of frames over 45 min-60 min) post-administration of $^{68}$Ga-Galuminox are shown in FIG. 7A. Pharmacokinetics were consistent with a dominant renal mode of probe excretion. Of note, $^{68}$Ga-Galuminox demonstrated a 5-fold higher uptake in lungs of LPS-treated (Standard Uptake Value; SUV: 12.9±1.85, n=4) C57Bl6 mice compared with their saline (vehicle) only treated counterparts (SUV: 2.62±0.48, n=4) (FIG. 7B). Finally, SUV time-activity curves (TACs) showed consistently higher and stable retention of $^{68}$Ga-Galuminox in lungs of LPS-treated mice (FIG. 7C) indicating retention of $^{68}$Ga-Galuminox in the injured lung, thus enabling PET imaging of endotoxin mediated insult in vivo.

Example 9

Figure 8:
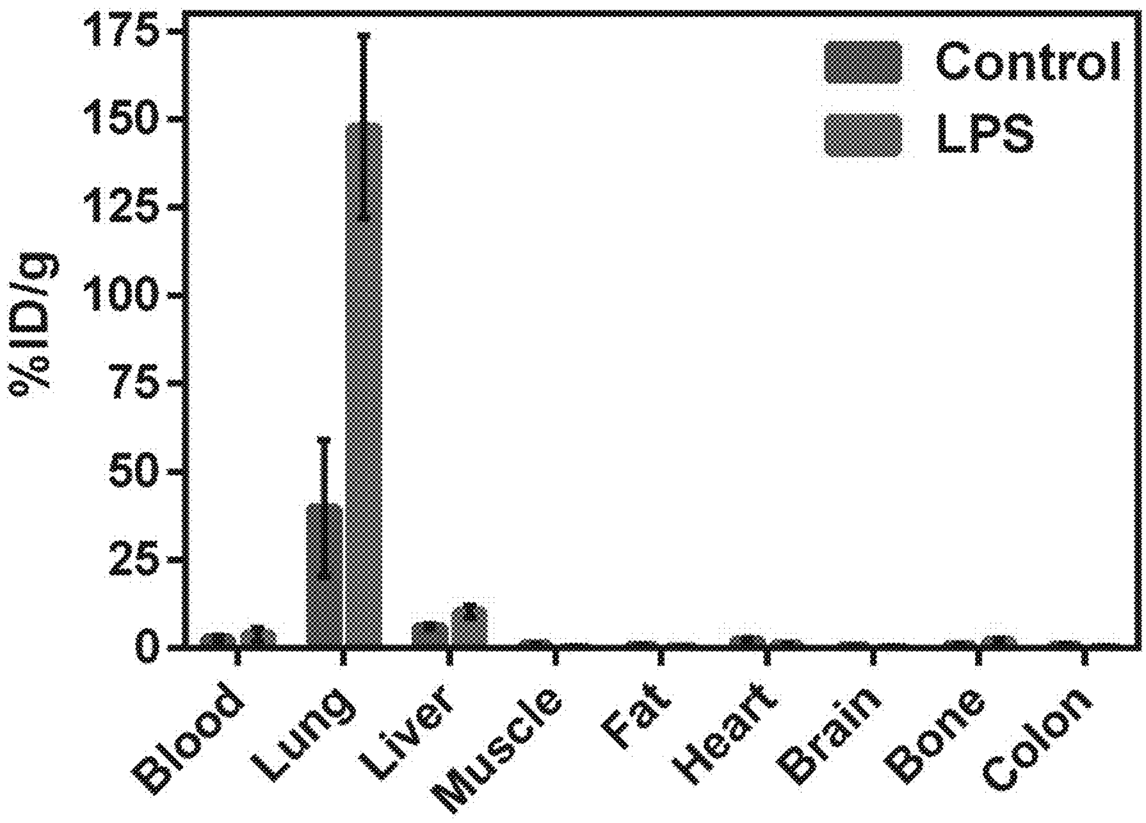
FIG. 8 depicts post-PET imaging biodistribution data (% ID/g) of B16 mice (24 h post-LPS treatment) and saline-treated controls. For each tissue type, control is the left column, and LPS is the right column.

For further correlating preclinical PET imaging data, post-imaging biodistribution studies were also conducted and percentage of activity that remained in critical tissues at 1-h post injection of the radiotracer is shown in FIG. 8. $^{68}$Ga-Galuminox demonstrated excretion profiles mediated by both hepatobiliary- and renal-modes of excretion. Compared with the saline-only treated mice (% ID/g: 39.7±19.3), the radiotracer was retained 4-fold higher in lungs of LPS treated mice (% ID/g: 147.9±25.8). The radiotracer also showed 1.4-fold higher retention in the blood of LPS treated mice (% ID/g: 3.96±1.83) compared with their saline-treated counterparts ((% ID/g: 2.82±0.88) as shown in Table 2. The latter was consistent with expected LPS-induced activation of ROS within neutrophils. For assessing specific retention of the radiotracer within the lung tissue, the activity in the lung (4 fold) was normalized to that of blood (1.4 fold) for LPS treated mice and indicated 3 (4/1.4=2.85) fold higher specific retention in lungs of LPS treated mice (Table 2). Additionally, LPS-induced effects were also observed in the liver (% ID/g: 10.5±1.68 (LPS); 6.14±0.66 (Saline); 1.7 fold) and bone (% ID/g: 2.14±0.57 (LPS); 1.0±0.34 (Saline); 2.1 fold) likely attributed to ROS mediated hepatotoxicity and ROS upregulation in bone marrow macrophages, respectively, thus indicating systemic effect following administration of endotoxin.

Example 10

Figure 9:
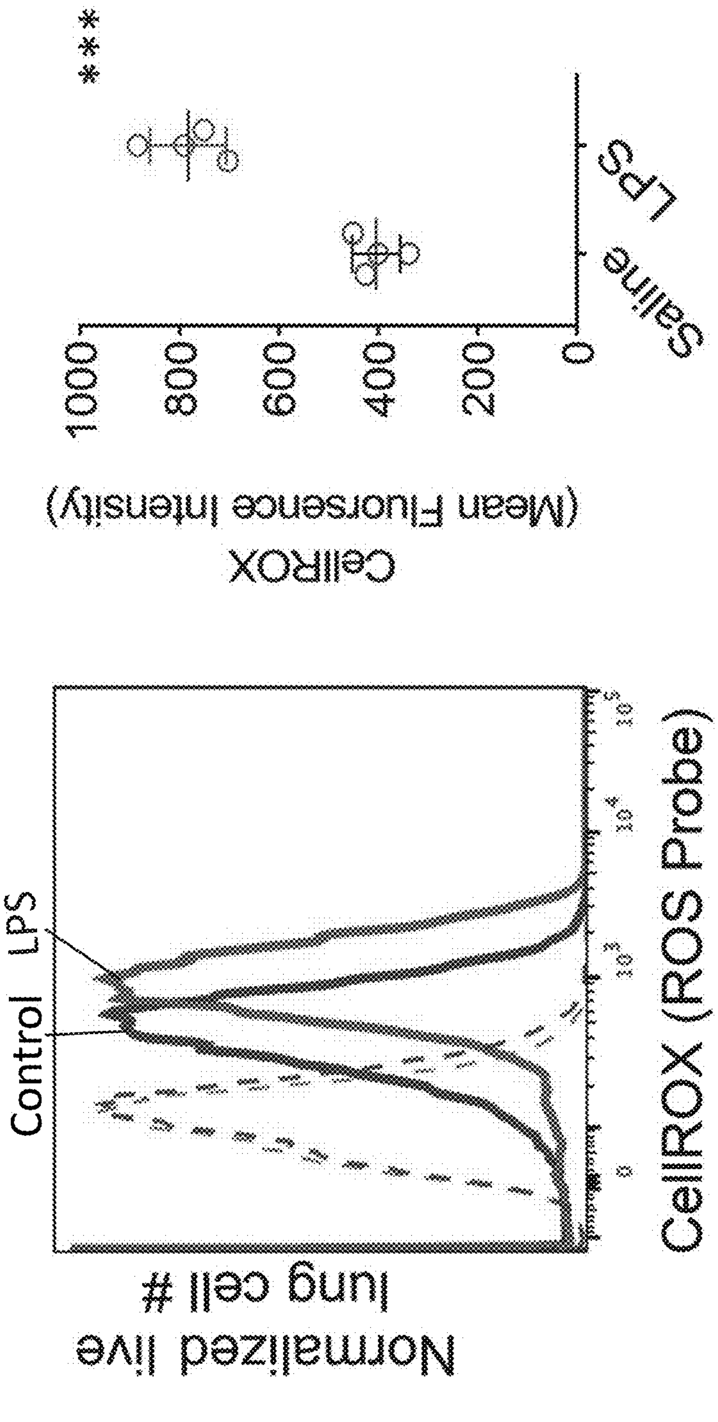
FIG. 9 depicts lung cell ROS generation measurement with CellROX. C57Bl6 mice (n=4/group) were injected with either LPS or saline intraperitoneally and euthanized 24 post-treatment. A single cell lung suspension was stained with 5 μM of CellROX green for 30 min at room temperature and assessed for mean fluorescence intensity (MFI) by flow cytometric analysis (FACS). FACS histogram plot (left) are representative measurements from saline (control) and LPS treated mice where dotted lines show background MFI (unstained) and solid lines show CellROX probed mice. Scatter plot on the right show MFI measurements for individual mice along with a group mean MFI±SEM where ***$p<0.001$ as determined by an unpaired student t-test.

To confirm pulmonary ROS generation in LPS-treated mice whole lung tissue was disrupted into single cell preparations and stained with CellROX Green, a well-established fluorescent probe that quantitates total ROS generation in live cells. CellROX Green (absorption/emission maxima of ~485/520 nm) is a cell-permeant weakly fluorescent dye in a reduced state and exhibits a bright green photostable fluorescence following oxidation by ROS and subsequent trapping within intracellular compartments. Lung cells were quantified for CellROX oxidation by measuring the mean fluorescence emission intensity (MFI) of between 515 and 545 nm following excitation with a 488 nm laser using a flow cytometer. An approximately two-fold higher ROS activity was observed in lung cells of LPS treated mice when compared to their counterparts that received saline as a vehicle (FIG. 9).

Example 11

Figure 10A:
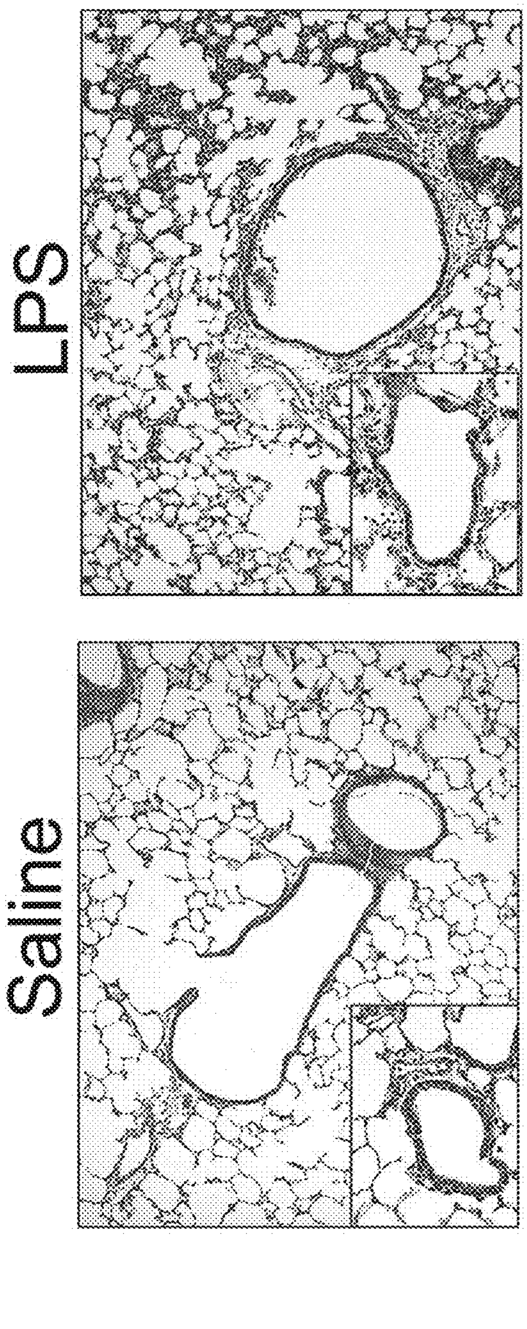
FIG. 10A depicts H&E lung histology in LPS mediated acute lung injury. C57Bl6 mice (n=4/group) were injected with either LPS or saline intraperitoneally and euthanized 24 post-treatment. H&E lung histology (100× and 400× inset) from a representative mouse from each group.
Figure 10B:
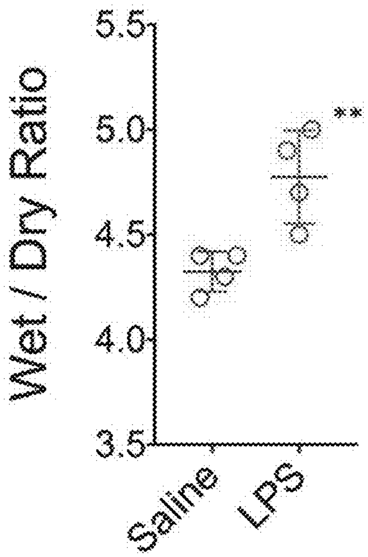
FIG. 10B depicts lung wet to dry ratio in LPS mediated acute lung injury. C57Bl6 mice (n=4/group) were injected with either LPS or saline intraperitoneally and euthanized 24 post-treatment. Lung wet to dry ratio is shown for individual mice and as a mean±SEM where **$p<0.01$ and *$p<0.05$ as determined by an unpaired student t-test.
Figure 10C:
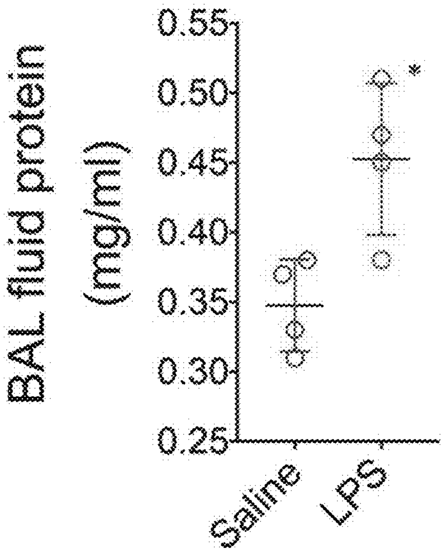
FIG. 10C depicts BAL fluid protein content in LPS mediated acute lung injury. C57Bl6 mice (n=4/group) were injected with either LPS or saline intraperitoneally and euthanized 24 post-treatment. BAL fluid protein content is shown for individual mice and as a mean±SEM where **$p<0.01$ and *$p<0.05$ as determined by an unpaired student t-test.

ROS injures lung tissue by disrupting hemostatic barriers that lead to pulmonary edema through breaking down endothelial cell tight junctions and triggering epithelial cell necrosis. Therefore, it was interrogated if Galuminox uptake was associated with histological and physiological evidence of acute injury. Hemotoxylin and Eosin staining of lungs of LPS-treated mice revealed polynuclear infiltration and thickening of the alveolar epithelial membranes (FIG. 10A). Analysis of lung tissue wet to dry ratio and bronchioalveolar lavage protein content, both measures of pulmonary edema, were both significantly elevated in LPS-treated mice (FIGS. 10B & C). Taken collectively, these data indicate that Galuminox uptake is a measure of ROS generation following ALI.

Example 12

Figure 11:
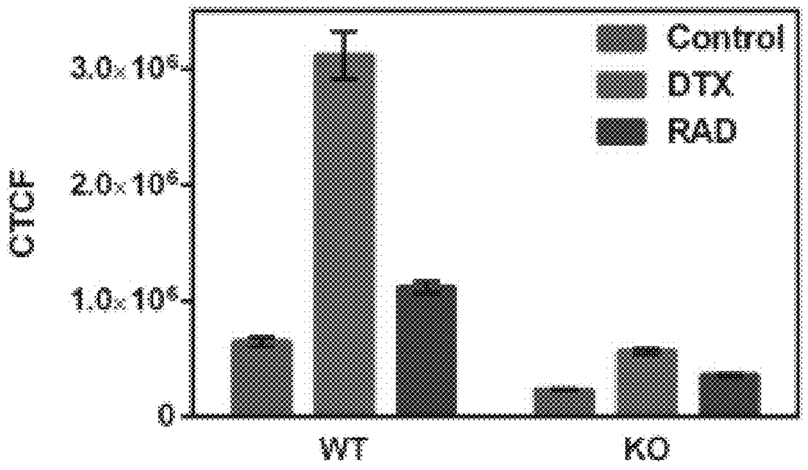
FIG. 11 depicts the ability of Galuminox to evaluate β-3 integrin induced chemoresistance. Wild type (WT) and 0-3 knock out (KO) triple negative 4T1 breast cancer cells were treated with a control, docetaxel (DTX), or Everolimus (RAD). Cells were fluorescently stained for reactive oxygen species (ROS) by Galuminox. Corrected total cell fluorescence (CTCF) was quantified. For each condition, the labels from top to bottom correspond to the columns from left to right.

Next the ability of Galuminox to evaluate β-3 integrin induced chemoresistance was explored. Wild type (WT) and β-3 knock out (KO) triple negative 4T1 breast cancer cells were treated with a control, docetaxel (DTX), or Everolimus (RAD), an mTOR inhibitor. Cells were fluorescently stained for reactive oxygen species (ROS) by Galuminox, and corrected total cell fluorescence (CTCF) was quantified (FIG. 11). Galuminox showed a response to integrin 0-3 mediated signaling and was also used to monitor the efficacy of Everolimus, an mTor inhibitor.

Example 13

Lung transplant recipients live approximately half as long as other solid organ recipients mainly due to the development of Chronic Lung Allograft Dysfunction (CLAD). CLAD largely manifests itself as Obliterans Bronchiolitis (OB), which is characterized by extraluminal fibrotic airway lesions that inhibit oxygen exchange. OB lesions often grow progressively leading to the complete failure of the transplant. Notably, OB lesions are currently clinically evaluated by tissue biopsy. However, OB lesions, due to sporadic and non-uniform development, are often not detected prior to the significant loss of lung function or graft failure. Also, biopises cannot be continually extracted to monitor disease progression given the risk for internal bleeding. Therefore, there is a need for non-invasive imaging techniques that better validate CLAD pathogenesis and identify patients who are at potentially risk for developing CLAD.

The next experiment was an evaluation of Galuminox in a mouse lung transplant model of CLAD. Allogeneic (FVB) left lung recipients (B16 mice) were treated with immunosuppression agents CD40L and CTLA4Ig to induce tolerance. Despite treatment with immunosuppressant drugs, allogeneic transplants show OB lesions as a function of time, normally defined as early stages of disease progression (early CLAD) and late stages of disease progression (fulminant CLAD).

Figure 12A:
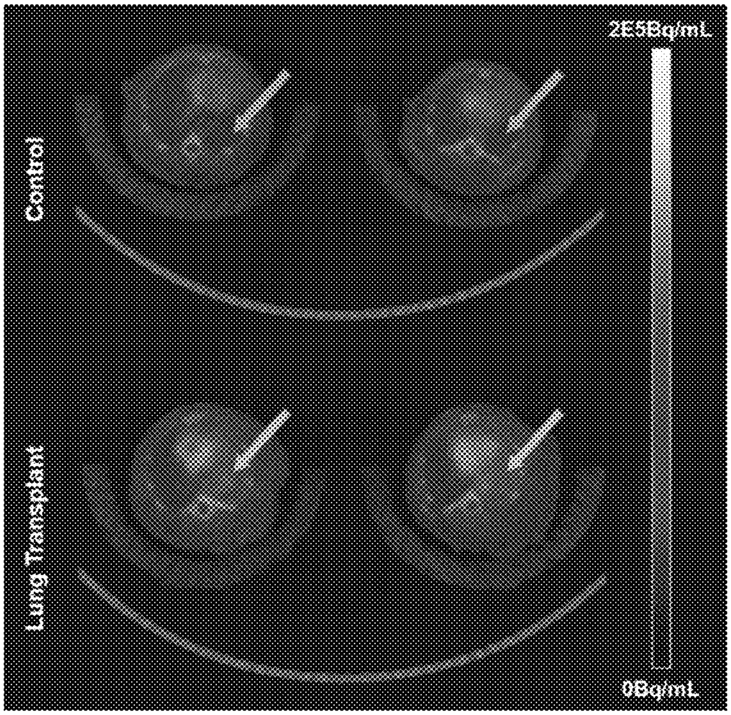
FIG. 12A depicts MicroPET/CT imaging 4 days post left lung transplant from FVB mice (donor) into B16 mice (acceptor). Both transplanted mice (Bottom) and non-transplanted control (Top) counterparts were imaged using PET/CT 30 minutes post tail-vein administration of $^{68}$Ga-Galuminox, deploying static acquisition scan of 20 min. PET images were co-registered with CT for anatomical correlation.
Figure 12B:
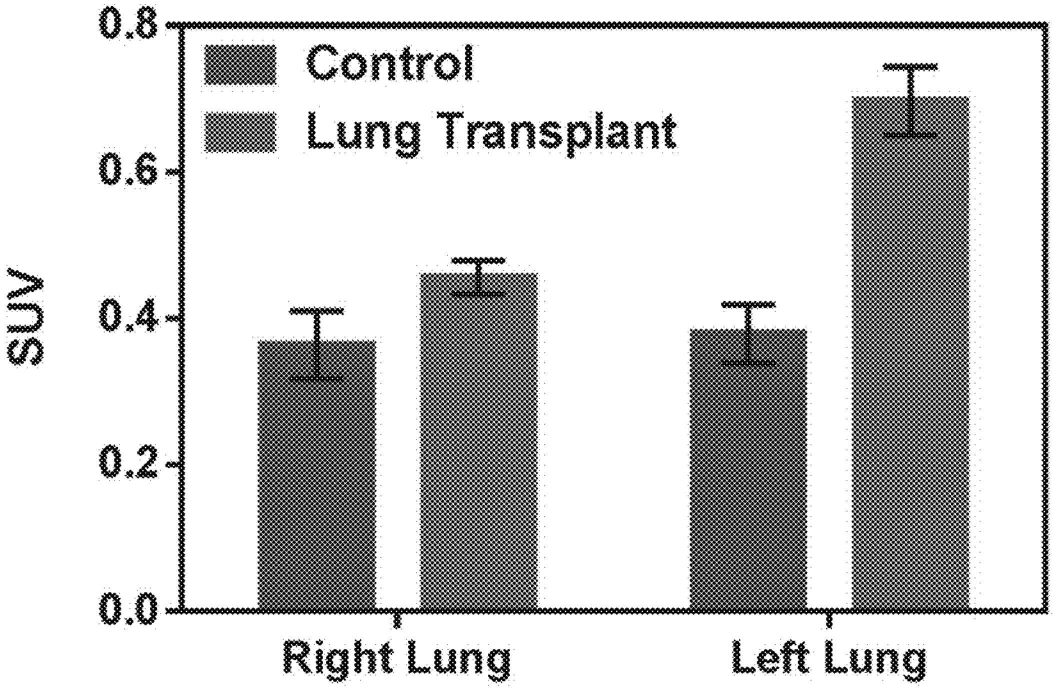
FIG. 12B depicts the quantification of Standard Uptake Values (SUVs) from the data depicted in FIG. 12A. SUVs were determined by drawing ROI, and counts were normalized to injected dose and weights of animals. For each lung, the labels from top to bottom correspond to the columns from left to right.

4 days post left lung transplant from FVB mice (donor) into B16 mice (acceptor), both transplanted mice and untransplanted control counterparts were imaged using PET/CT 30 minutes post tail-vein administration of $^{68}$Ga-Galuminox using static acquisition scan of 20 min (FIG. 12A). PET images were co-registered with CT for anatomical correlation. Standard Uptake Values (SUVs) were determined by drawing ROI, and counts were normalized to injected dose and weights of animals (FIG. 12B). Compared with untransplanted B16mice, $^{68}$Ga-Galuminox shows 1.5-fold higher uptake in the left transplanted lung as an indication of detection of early CLAD. Furthermore, same differentiation in retention of the activity was observed in left transplanted lung compared with its right lung (control) within the same mice.

Example 14

Figure 13:
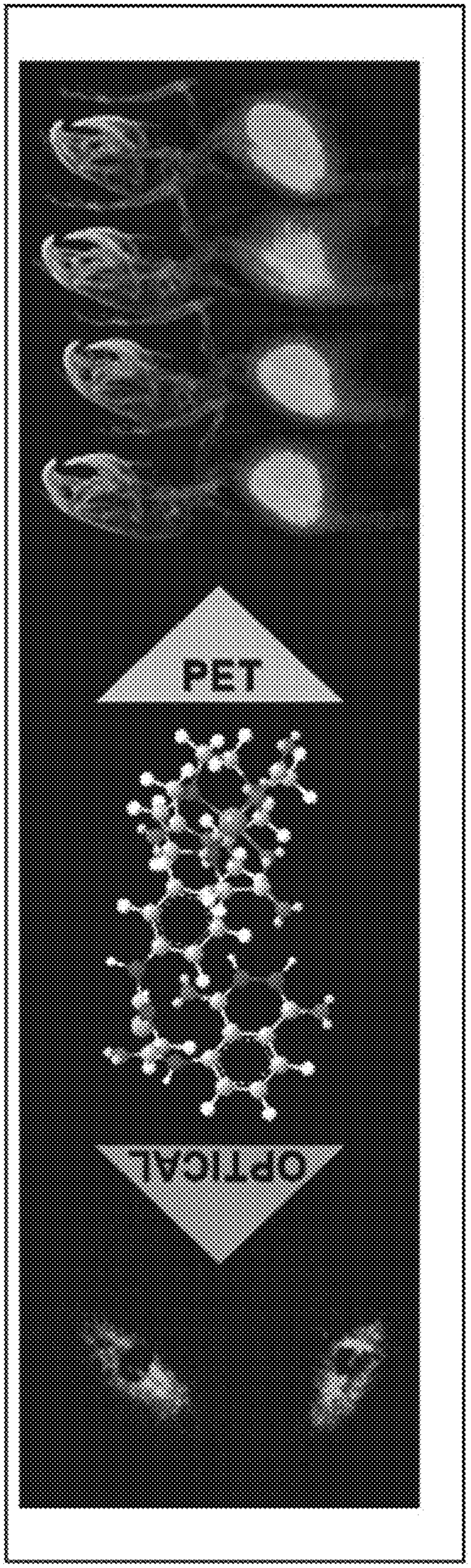
FIG. 13 depicts a graphical abstract for the experiments of the present invention.

A graphical abstract to summarize aspects of the invention is shown (FIG. 13). Galuminox can be used for both PET and optical imaging of oxidative stress.

What is claimed is:

1. An imaging agent, wherein the imaging agent is a compound of formula (IIa) or (IIb):

(IIa)

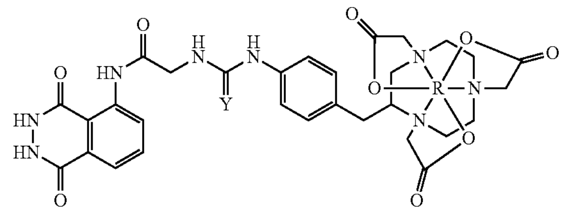

(IIb)

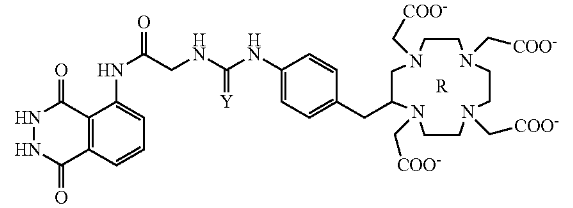

where R is a radiometal; and Y is O or S; or a compound of formula (IIIa) or (IIIb):

(IIIa)

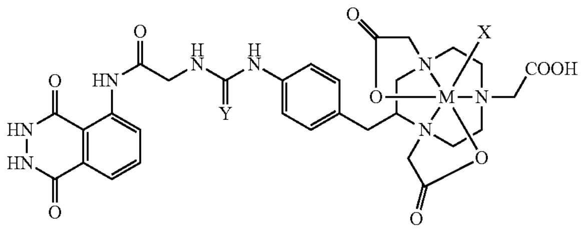

-continued (IIIb)

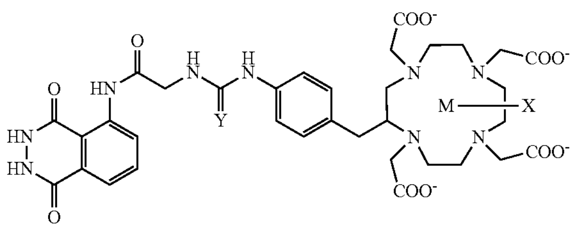

where M-X is the radiolabeled component with M is a metal and X is a halogen radioisotope, and Y is O or S.

2. The imaging agent of claim 1, wherein the imaging agent is:

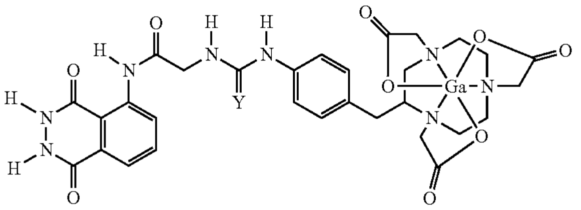

wherein Ga in the formula is $^{68}$Ga or $^{67}$Ga.

3. The imaging agent of claim 1, wherein the imaging agent is:

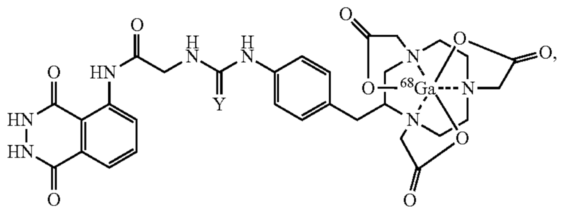

wherein Y is O or S.

4. The imaging agent of claim 1, wherein the imaging agent is a magnetic resonance imaging (MRI) contrast agent, a positron emission tomography (PET) imaging agent, a single-photon emission computerized tomography (SPECT) imaging agent, or a PET-MRI imaging agent.

5. The imaging agent of claim 1, wherein the imaging agent is capable of targeting or imaging oxidative stress, reactive oxygen species (ROS), superoxide generation, or hydrogen peroxide generation.

6. A pharmaceutical composition comprising the imaging agent of claim 1 and one or more pharmaceutically acceptable carriers and/or excipients.

7. A method of detecting reactive oxygen species (ROS) or imaging reactive oxygen species (ROS) mediated pathophysiology in a subject comprising:

administering a detectable amount of an imaging agent according to claim 1; and detecting the imaging agent or radiation thereof to identify and/or quantify the ROS.

8. A method of imaging reactive oxygen species (ROS) in a subject or region of a subject comprising:

administering the imaging agent, according to claim 1; and detecting the imaging agent or radiation thereof to identify and/or quantify the ROS, wherein the method of imaging is PET, PET-MRI, MRI, or single-photon emission computed tomography (SPECT).

9. The method of claim 8, wherein the region of the subject is an organ or organ system.

10. The method of claim 9, wherein the organ comprises a lung.

11. The method of claim 8, wherein the subject is being treated for, has, or is suspected of having inflammation, ischemia, tissue injury, acute lung injury, chronic lung allograft dysfunction, oxidative stress-induced inflammation within lungs, and/or oxidative stress in other diseases selected from the group consisting of tissue inflammation, cardiovascular disease, diabetes, atherosclerosis, asthma, Alzheimer's disease, psoriasis, rheumatoid arthritis, aging, acute lung injury (ALI), cancer, and breast cancer.

12. The imaging agent of claim 1, wherein the imaging agent is:

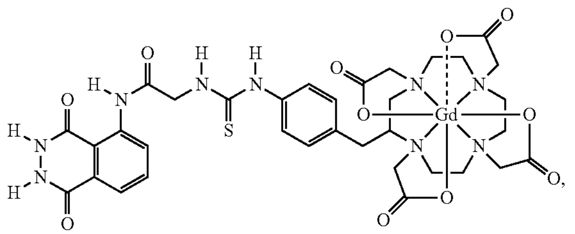

wherein Gd in the formula is $^{153}$Gd.

13. The imaging agent of claim 1, wherein R or M is selected from the group consisting of $^{22}$Na, $^{26}$Al, $^{38}$K, $^{40}$K, $^{52}$Fe, $^{55}$Co, $^{62}$Zn, $^{63}$Zn, $^{63}$Zn, $^{61}$Cu, $^{62}$Cu, $^{64}$Cu, $^{67}$Cu, $^{67}$Ga, $^{68}$Ga, $^{82}$Rb, $^{89}$Zr, $^{89}$Sr, $^{86}$Y, $^{90}$Y, $^{94}$Tc, $^{99}$Tc, $^{110}$In, $^{111}$ In, $^{153}$ Gd, $^{155}$Tb, $^{177}$Lu, $^{186}$Re, $^{188}$Re, and $^{201}$Tl.

14. The imaging agent of claim 1, wherein R or M is selected from the group consisting of $^{22}$Na, $^{26}$ Al, $^{82}$Rb, $^{38}$K, $^{62}$Cu, $^{63}$Zn, $^{68}$Ga, $^{61}$Cu, $^{52}$Fe, $^{62}$Zn, $^{64}$Cu, $^{86}$Y, $^{55}$Co, $^{68}$Ge, $^{40}$K, $^{110}$In, $^{94}$Tc, and $^{89}$Zr.

15. The imaging agent of claim 1, wherein R or M is selected from the group consisting of $^{68}$Ga, $^{67}$Ga, $^{99m}$Tc, and $^{111}$In.

16. The imaging agent of claim 1, wherein X is selected from the group consisting of $^{18}$F, $^{36}$Cl, $^{75}$Br, $^{76}$Br, $^{77}$Br, $^{82}$Br, $^{122}$Xe, $^{120}$I, $^{121}$I, $^{123}$I, $^{124}$I, $^{125}$I, and $^{131}$I.

17. The imaging agent of claim 1, wherein X is selected from the group consisting of $^{18}$F, $^{76}$Br, $^{121}$I, $^{120}$I, and $^{124}$I.

18. The imaging agent of claim 1, X is selected from the group consisting of $^{18}$F, $^{123}$I, and $^{131}$I.

19. The imaging agent of claim 1, wherein R is $^{68}$Ga or M-X is Al$^{18}$F.

20. The imaging agent of claim 1, where M is a transition metal ion or a metal ion of groups 8-13.

* * * * *